United States Patent
Frater

(10) Patent No.: US 9,399,105 B2
(45) Date of Patent: Jul. 26, 2016

(54) MASK SYSTEM

(75) Inventor: Robert Frater, Bella Vista (AU)

(73) Assignee: ResMed Limited, Bella Vista (AU)

( * ) Notice: Subject to any disclaimer, the term of this patent is extended or adjusted under 35 U.S.C. 154(b) by 150 days.

(21) Appl. No.: 13/138,575

(22) PCT Filed: Apr. 1, 2010

(86) PCT No.: PCT/AU2010/000381
§ 371 (c)(1),
(2), (4) Date: Sep. 7, 2011

(87) PCT Pub. No.: WO2010/111749
PCT Pub. Date: Oct. 7, 2010

(65) Prior Publication Data
US 2011/0315143 A1    Dec. 29, 2011

Related U.S. Application Data

(60) Provisional application No. 61/202,779, filed on Apr. 3, 2009.

(51) Int. Cl.
*A61M 16/06* (2006.01)

(52) U.S. Cl.
CPC ............ *A61M 16/0683* (2013.01); *A61M 16/06* (2013.01); *A61M 16/065* (2014.02); *A61M 16/0616* (2014.02); *A61M 16/0638* (2014.02); *A61M 16/0611* (2014.02); *A61M 16/0666* (2013.01)

(58) Field of Classification Search
CPC ............ A61M 16/06; A61M 16/0611; A61M 16/0616; A61M 16/0638; A61M 16/065; A61M 16/0666; A61M 16/0683; A61M 2205/33; A61M 2205/3331; A61M 2210/0618; A61M 2210/0625
USPC ............. 128/204.18, 205.24, 205.25, 206.21, 128/206.24, 206.26, 206.28, 207.11, 207.13
See application file for complete search history.

(56) References Cited

U.S. PATENT DOCUMENTS

| 1,873,160 | A | | 8/1932 | Sturtevant | |
| 5,243,972 | A | * | 9/1993 | Huang | 128/205.25 |
| 5,265,595 | A | * | 11/1993 | Rudolph | 128/204.18 |
| 5,560,354 | A | | 10/1996 | Berthon-Jones et al. | |

(Continued)

FOREIGN PATENT DOCUMENTS

| EP | 0634186 A2 | 1/1995 |
| GB | 1909-01085 A | 12/1909 |

(Continued)

OTHER PUBLICATIONS

International Search Report issued in PCT/AU2010/000381, mailed Aug. 9, 2010.

(Continued)

*Primary Examiner* — Justine Yu
*Assistant Examiner* — Timothy Stanis
(74) *Attorney, Agent, or Firm* — Nixon & Vanderhye, P.C.

(57) ABSTRACT

A nasal mask system includes an interface (80) adapted to form an air interface with a patient's nose, and a mouth seal (10) adapted to form a seal (20) with the patient's mouth. The mouth seal (20) is communicated with the interface (80) via a one-way air path (40) that allows exhausted air from the mouth seal to pass into the interface (80) but prevents air from the interface (80) from passing into the mouth seal (10).

31 Claims, 24 Drawing Sheets

(56) References Cited

U.S. PATENT DOCUMENTS

| | | | |
|---|---|---|---|
| 5,596,983 | A | 1/1997 | Zander et al. |
| 6,123,082 | A | 9/2000 | Berthon-Jones |
| 6,571,798 | B1 | 6/2003 | Thornton |
| 6,581,594 | B1 * | 6/2003 | Drew et al. ............... 128/204.18 |
| 7,669,599 | B2 | 3/2010 | Gunaratnam et al. |
| 7,814,914 | B2 | 10/2010 | Lang et al. |
| 2004/0118406 | A1 | 6/2004 | Lithgow et al. |
| 2004/0226563 | A1 * | 11/2004 | Xu et al. ................... 128/206.21 |
| 2006/0005837 | A1 * | 1/2006 | Thornton ................. 128/205.25 |
| 2006/0054168 | A1 | 3/2006 | Yu |
| 2007/0006879 | A1 * | 1/2007 | Thornton ................. 128/203.29 |
| 2008/0135050 | A1 | 6/2008 | Hitchcock et al. |
| 2009/0044808 | A1 | 2/2009 | Guney et al. |
| 2009/0065729 | A1 | 3/2009 | Worboys et al. |
| 2009/0114229 | A1 | 5/2009 | Frater et al. |
| 2009/0183734 | A1 | 7/2009 | Kwok et al. |

FOREIGN PATENT DOCUMENTS

| | | |
|---|---|---|
| GR | 1003277 B1 | 12/1999 |
| WO | WO 2005/063378 | 7/2005 |
| WO | WO 2006/113321 | 10/2006 |
| WO | WO 2007/025329 | 3/2007 |

OTHER PUBLICATIONS

"Effect of nasal or oral breathing route on upper airway resistance during sleep"; M.F. Fitzpatrick, H. McLean, A.M. Urton, A. Tan, D. O'Donnell, H.S. Driver. #ERS Journals Ltd 2003; 22: 827-832.

Dec. 1, 2015 Supplementary Partial European Search Report issued in European Application No. 10757949.2.

Mar. 18, 2016 Extended European Search Report issued in European Application No. 10757949.2.

* cited by examiner

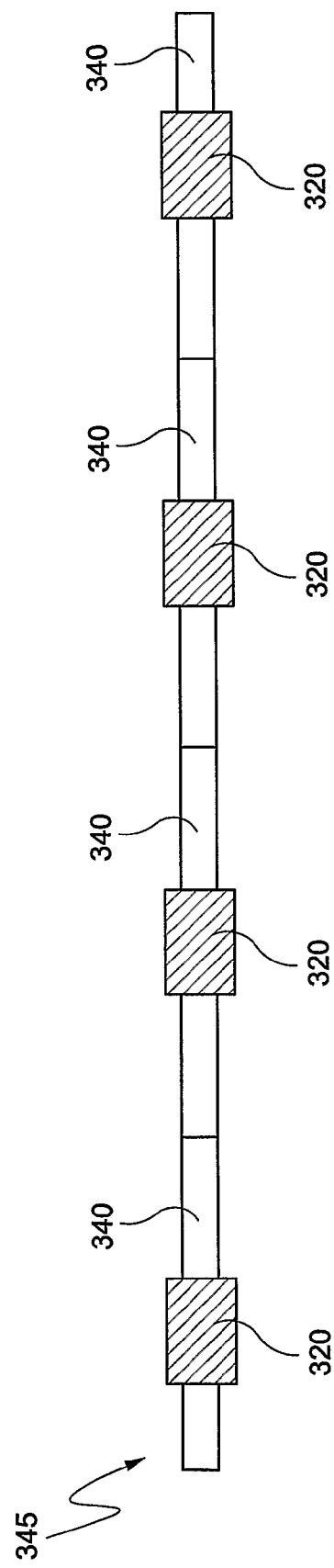

MASK SYSTEM

CROSS-REFERENCE TO APPLICATION

This application is a U.S. national phase of International Application No. PCT/AU2010/000381, filed Apr. 1, 2010, which designated the U.S. and claims the benefit of U.S. Provisional Patent Application No. 61/202,779, filed Apr. 3, 2009, which is incorporated herein by reference in its entirety.

FIELD OF THE INVENTION

The present technology relates to a mask system used for treatment of respiratory disorders, e.g., of Sleep Disordered Breathing (SDB) with Continuous Positive Airway Pressure (CPAP) or Non-Invasive Positive Pressure Ventilation (NIPPV).

BACKGROUND OF THE INVENTION

Treatment of sleep disordered breathing (SDB), such as obstructive sleep apnea (OSA), by continuous positive airway pressure (CPAP) mask systems involves the continuous delivery of air (or other breathable gas) pressurized above atmospheric pressure to the airways of a human or other mammalian patient via a conduit and a mask. Typically, the mask fits over the nose and/or mouth of the patient. Pressurized air flows to the mask and to the airways of the patient via the nose and/or mouth. As the patient exhales, carbon dioxide gas may collect in the mask. A washout vent in the mask or conduit discharges the exhaled gas from the mask to atmosphere.

Measures such as an Apnea-Hypopnea Index (AHI) are sometimes used to quantify the number of apneas and or hypopneas that a patient exhibits during a time period, as a measure of the severity of the condition. An AHI of about 5 is typically a low value, whereas an AHI of about 20 is a relatively high value. A patient with a high AHI value might need to change treatment, for example, to increase a CPAP treatment pressure.

Design of masks is a subtle art. Many patients find masks uncomfortable and they do not comply with therapy. Some masks are difficult to seal on the face, leading to patient tightening of retaining straps and this in turn can decrease comfort and lead to marks or sores on a patient's face. Some masks may exacerbate the problem they are trying to solve.

SUMMARY OF THE INVENTION

A first aspect of the present technology is a mask system that reduces the likelihood of a patient having obstructive apneas. Another aspect of the present technology is a mask system that reduces the treatment pressure required for patients to overcome obstructive apneas. Another aspect of the present technology is a mask system that reduces, or at least does not increase the Apnea-Hypopnea index of patients.

In one form, the present technology contemplates a mask system that places little or no backward or rearward force on the jaw. In another form of the present technology, a mask system is provided that reduces or eliminates mouth breathing. In one form of the present technology, a mask system is provided that reduces or eliminates mouth breathing while placing little or no backward or rearward force on the jaw.

Another aspect of the present technology is a mask system that promotes nasal breathing over mouth breathing.

An aspect of the present technology is a mask system constructed and arranged to reduce mouth breathing. In one form the mask system is configured to direct air exhaled from the mouth to a cavity surrounding an entrance to the nasal passages. In another form the mask system is configured to direct air exhaled from the mouth to a cavity surrounding an entrance to the nasal passages while preventing a flow of air from the cavity to the mouth.

Another aspect of the present technology relates to a mouth seal for use with a mask system that eliminates or at least minimizes mouth leak and/or mouth breathing.

Another aspect of the present technology relates to a nasal mask system including a nasal mask adapted to form a seal around the patient's nose and a mouth seal adapted to form a seal with the patient's mouth. The mouth seal is in airflow communication with the nasal mask via a one-way air path that allows exhausted air from the mouth seal to pass into the nasal mask but prevents pressurized air from the nasal mask from passing into the mouth seal.

Another aspect of the present technology relates to a full-face mask system including a full-face mask including a full-face cushion defining a breathing chamber to receive the patient's nose and mouth and including a membrane adapted to form a continuous seal around the patient's nose and mouth, and a mouth seal adapted to form a seal with the patient's mouth upon insertion of the patient's nose into the breathing chamber.

Another aspect of the present technology relates to a nozzle system including a nozzle assembly including a pair of nozzles structured to sealingly communicate with nasal passages of a patient's nose in use and a mouth seal adapted to form a seal with the patient's mouth. The nozzle assembly includes headgear to maintain the nozzle assembly in a desired position on the patient's face. The headgear includes side straps and rigidizers provided to respective side straps, and each rigidizer includes an extended portion to retain a respective end of the mouth seal.

Another aspect of the present technology relates to a mask system including a mask including a cushion adapted to form a seal around at least the patient's nose and a mouth seal adapted to form a seal with the patient's mouth. The mouth seal is formed in one piece with the cushion.

Another aspect of the present technology relates to a mouth seal for use with a mask system including a sealing portion positioned and arranged to apply force only over a limited range under the lower lip of the patient in use.

Another aspect of the present technology relates to a method of controlling air flow in a mask system by allowing air from a patient exhausted to a mouth seal to pass through an air conduit and into a nasal interface, while preventing air from the nasal interface from passing into the mouth seal.

Another aspect of the present technology relates to a method and system for promoting nasal breathing over mouth breathing for a user receiving treatment for obstructive sleep apnea, where pressure is equalized between an interface providing pressurized gas to the nasal openings of the user, and a mouth seal in close proximity to or in light contact with the user's mouth, if the pressure in a cavity of the mouth seal exceeds the pressure within the interface. In an alternative, cavity pressure of the mouth seal can be equalized with ambient/atmospheric pressure, e.g., via a valve or a similar mechanism provided to the mouth seal.

Other aspects, features, and advantages of the present technology will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIG. 1 is a schematic view of a mouth seal used in conjunction with a nasal mask according to an embodiment of the present technology;

FIG. 4b is a schematic view showing a process for manufacturing a mouth seal according to an embodiment of the present technology;

DETAILED DESCRIPTION OF ILLUSTRATED EMBODIMENTS

Figure 1A:
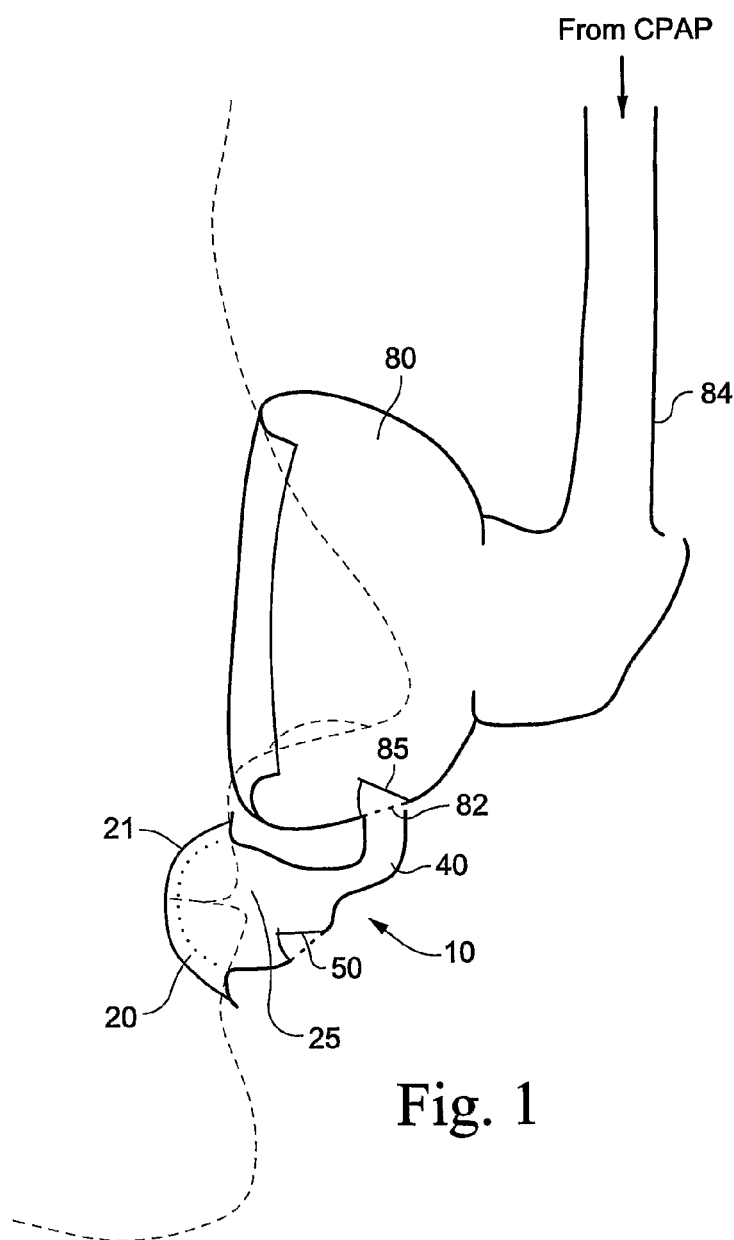
FIG. 1a is a schematic view showing the mouth seal of FIG. 1 in relation to the patient's mouth before sealing.

It has been found that upper airway resistance during sleep and the propensity to obstructive sleep apnea are significantly higher when patients breathe through their mouth than when they breathe through their nose. See "Effect of nasal or oral breathing route on upper airway resistance during sleep"; M. F. Fitzpatrick, H. McLean, A. M. Urton, A. Tan, D. O'Donnell, H. S. Driver. #ERS Journals Ltd 2003; 22: 827-832.

This situation can lead to patients requiring higher treatment pressures when using full-face masks (i.e., masks that deliver gas to the mouth and nose of the patient) to overcome airflow limitation compared to treatment pressures using nasal masks. Also, the full-face mask has to be held firmly against the cheeks and the lower jaw to seal. Such backward pressure on the lower jaw can cause discomfort and/or pain in the temporomandibular joint as the lower part of the full-face mask is tightened to effect a seal. Backward movement of the lower jaw can also reduce the airway size.

In addition, patients initially presented with a nasal mask, nozzles or nasal prongs who "mouth breathe" because of a blocked nose are commonly prescribed full-face masks rather than being instructed on how to clear their nasal passages. That is, if a patient with a blocked nose is encouraged to breathe through their mouth, they will have a higher Apnea-Hypopnea Index (AHI) and may need higher CPAP pressure to overcome this. Some APAP (Automatic Positive Airway Pressure) systems will not respond to such need for higher pressure.

When nasal masks are used, e.g., nasal masks, nozzles or nasal prong assemblies, some patients have a tendency for mouth leak meaning that air delivered to the patient from the PAP device is exhaled through the mouth, rather than the nose as intended. Alternatively or in addition, some patients may have a tendency for mouth breathing when using a nasal mask. When air escapes through the patient's mouth, the patient does not obtain the full benefit of the delivered treatment pressure. Therefore, the effectiveness of CPAP therapy is diminished. In addition, mouth leak may result in noise, increased treatment pressure to compensate for the leak, increased load on the nasal passages, nasal obstruction, and/or mucosal build up in the nose, for example.

The reduction of mouth leak and the prevention of mouth breathing encourage nasal breathing which may prove beneficial for the patient.

The following description is provided in relation to several embodiments or examples which may share common characteristics and features. It is to be understood that one or more features of any one embodiment or example may be combinable with one or more features of the other embodiments or examples. In addition, any single feature or combination of features in any of the embodiments or examples may constitute additional embodiments or examples.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen.

1. Mouth Seal

Embodiments of the present technology are directed towards a mouth seal for use with a mask system that eliminates or at least minimizes mouth leak and/or mouth breathing. The mouth seal may be retrofit to an existing mask system, or the mouth seal may be provided as original equipment or integrated with a mask system. The mouth seal may or may not include an anti-asphyxia valve. Also, the mouth seal may be supported by a mount that is separate from and/or integrated with the mask system and/or a strap arrangement.

Such mount may or may not be communicated with the breathing cavity of the mask system, e.g., via a one-way valve.

The mouth seal may be adapted for use with any suitable breathing arrangement, e.g., nasal mask, full-face mask, nozzle assembly, nasal assembly, nasal prongs, nasal pillows, nasal cannulae, nasal inserts, nozzles, etc.

1.1 Sealing Arrangement

The mouth seal includes a sealing portion positioned and arranged adjacent the patient's mouth so as to eliminate or at least minimize mouth leak and/or mouth breathing. As described below, the mouth seal uses inflation of the patient's lips and/or cheeks against the sealing portion to provide a seal. This arrangement is in contrast to mask cushion-type seals in which force of a cushion onto the patient's face is required to provide a seal.

1.1.1 Seal Around Mouth

Figure 1A:
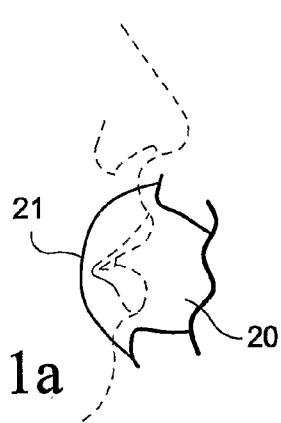
Figure 1B:
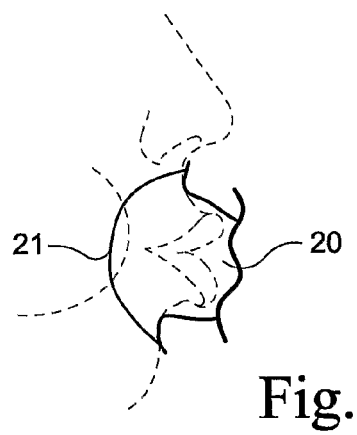
FIG. 1b is a schematic view showing the mouth seal of FIG. 1 in sealing relation with the patient's mouth.

In an embodiment, as shown in FIG. 1, the mouth seal 10 may include a sealing portion 20 structured to sealingly engage around an exterior of a patient's mouth in use. The face-contacting portion of the sealing portion 20 includes a membrane 21 that provides a sealing structure and defines a mouth seal cavity or chamber 25 to receive the patient's mouth. In use, when the patient has a tendency for mouth leak, the pressure inside the patient's mouth pushes the patient's lips and/or cheeks against the sealing portion 20. Thus, the patient's lips and/or cheeks conform to the mouth seal due to the differential pressure between the patient's mouth and the outside of the mouth seal. This arrangement enables an effective mouth seal completely around the patient's mouth, thereby eliminating or at least minimizing the loss of therapy effectiveness resulting from mouth leak. FIG. 1*a* shows the sealing portion 20 in relation to the patient's mouth before sealing, and FIG. 1*b* shows the sealing portion 20 engaged with the patient's mouth when differential pressure pushes the patient's lips and/or cheeks against the sealing portion. In FIG. 1, the sealing portion 20 may be closely adjacent to or in light sealing contact with the patient's mouth, so as to not apply excessive rearward force, if any, to the patient's mouth region, especially so as not to apply such rearward force to the patient's lower jaw. This avoids the backward displacement of the patient's lower jaw, which could reduce the size of the patient's airways, reducing the effectiveness of the therapy and/or potentially requiring increased pressure to achieve the same therapeutic effect.

As shown in FIG. 1, the membrane 21 may provide an arcuate or rolled-over shape that curves away from the interior of the cavity 25. However, the membrane may have other suitable shapes adapted to contact the patient's face, e.g., bulbous shape or intraoral structure as described in U.S. application Ser. No. 11/794,178, filed Jul. 26, 2007, which is incorporated herein by reference in its entirety.

Figure 11:
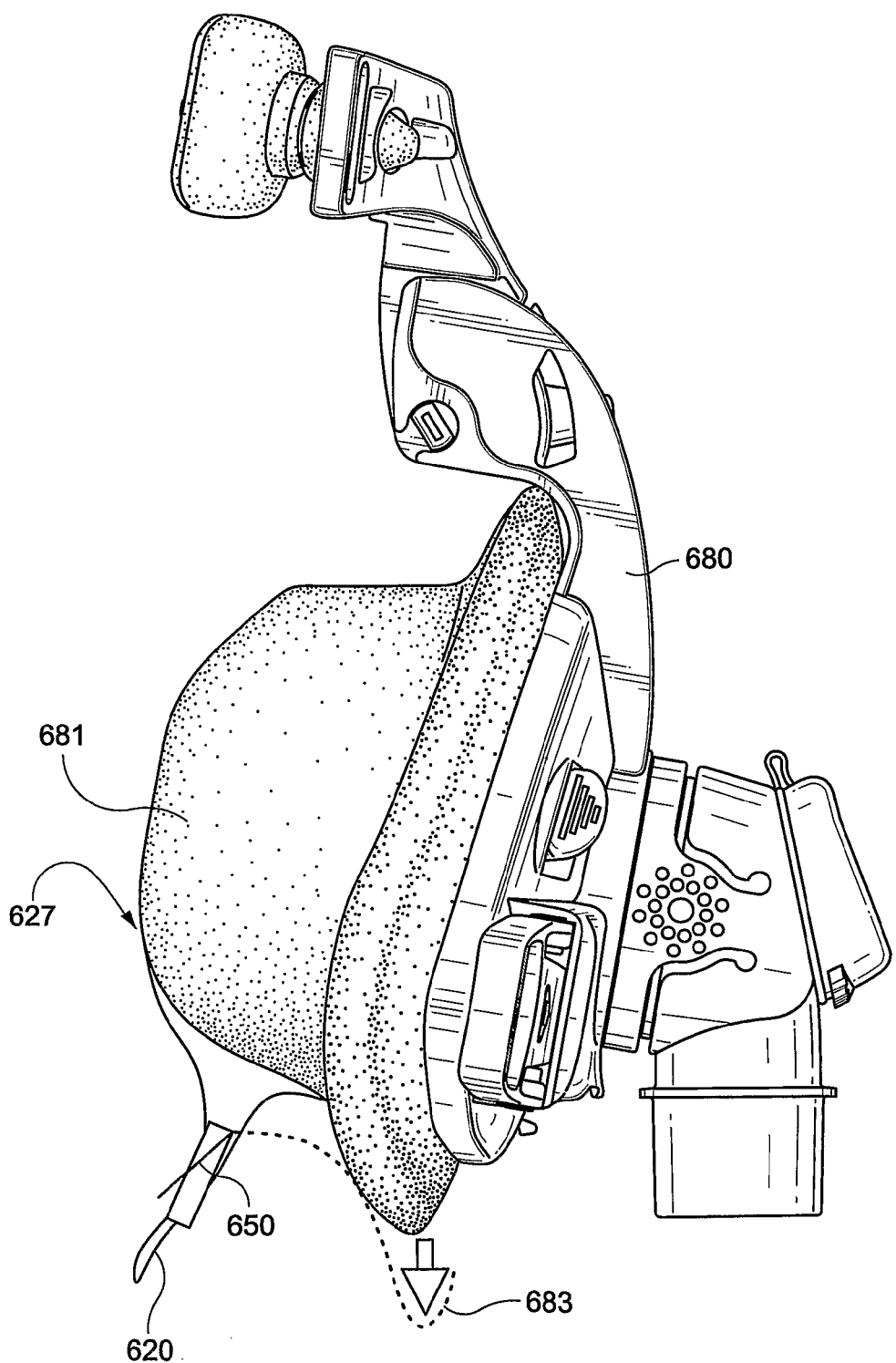
FIG. 11 is a side view of a mouth seal used in conjunction with a nasal mask according to another embodiment of the present technology.
Figure 11B:
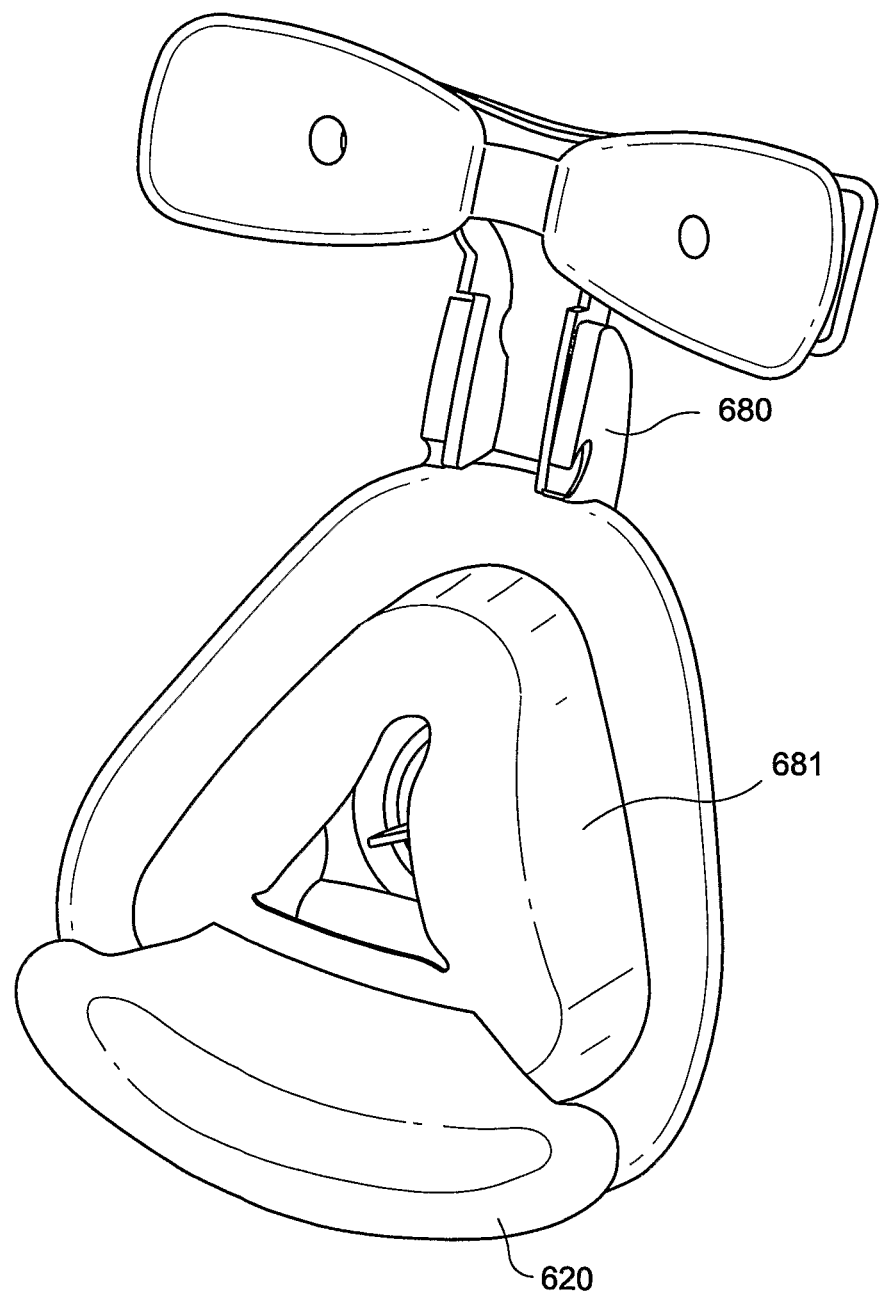
FIG. 11B is a perspective view of the mouth seal and mask of FIG. 11.
Figure 12:
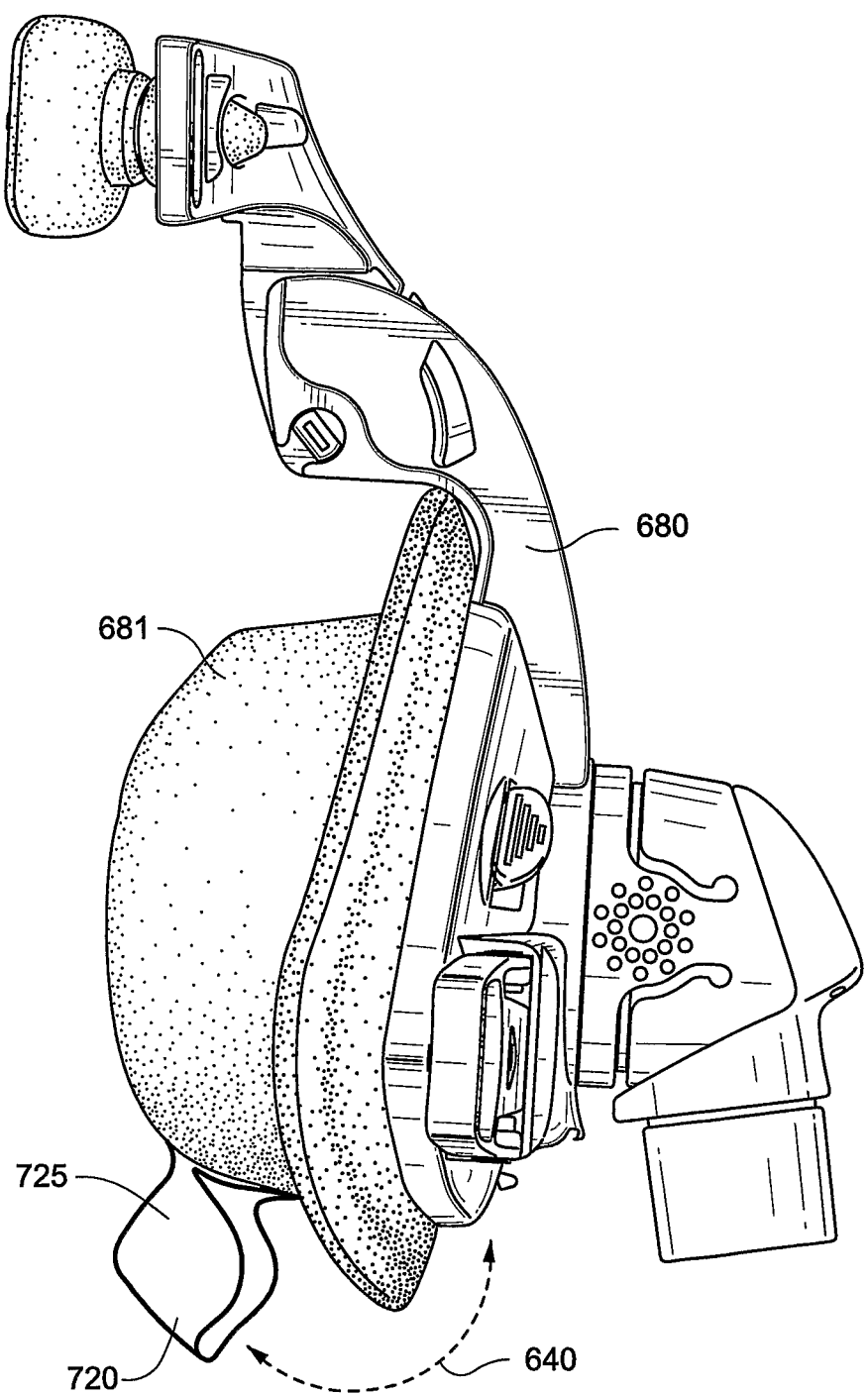
FIG. 12 is a schematic side view of a mouth seal used in conjunction with a nasal mask according to another embodiment of the present technology.
Figure 12B:
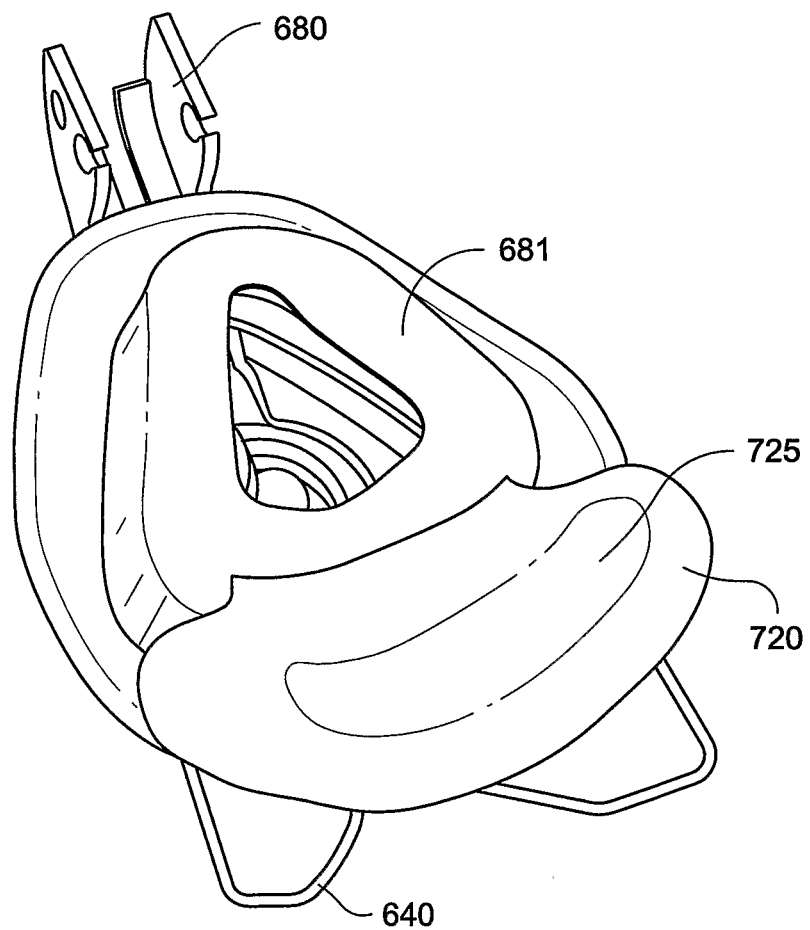
FIG. 12B is a perspective view of the mouth seal and mask of FIG. 12.
Figure 13:
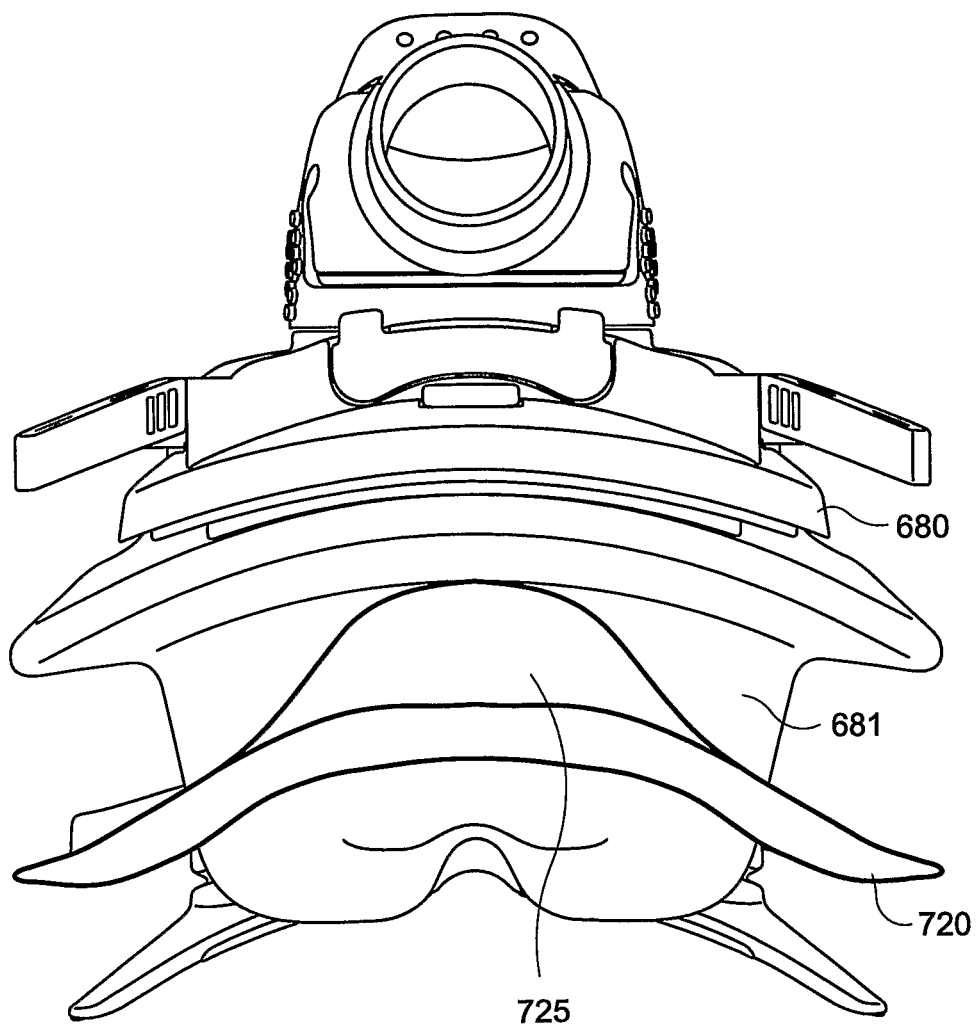
FIG. 13 is a schematic bottom view of the mouth seal and mask of FIG. 12.

Other examples of mouth seals including such a sealing portion adapted to seal around the patient's mouth are shown in FIGS. 11-13. For example, the mouth seal 620 of FIGS. 11 and 11B is tapered along its length and the mouth seal 720 of FIGS. 12, 12B, and 13 includes a cavity 725 that tapers along cheek portions thereof.

In an embodiment, the mouth seal may be relatively narrow to allow the patient to open their mouth beyond the edge of the seal when not in use, e.g., to talk or breathe.

1.1.2 Adjacent Lower Lip

In an alternative embodiment, the sealing portion may be placed under the lower lip of the patient. In use, this arrangement will provide an upwards force to the lower lip of the patient, thereby increasing the contact force between the patient's lips. Such contact force will increase the effort required to open the mouth and potentially create a more effective seal between the patient's lips. Accordingly, this arrangement makes it more difficult for air to pass between the lips of the patient and thus eliminate or reduce the incidence of mouth leak. In a preferred form, the sealing portion is constructed and arranged to reduce mouth breathing without applying a rearward or backward force to the jaw.

Figure 2:
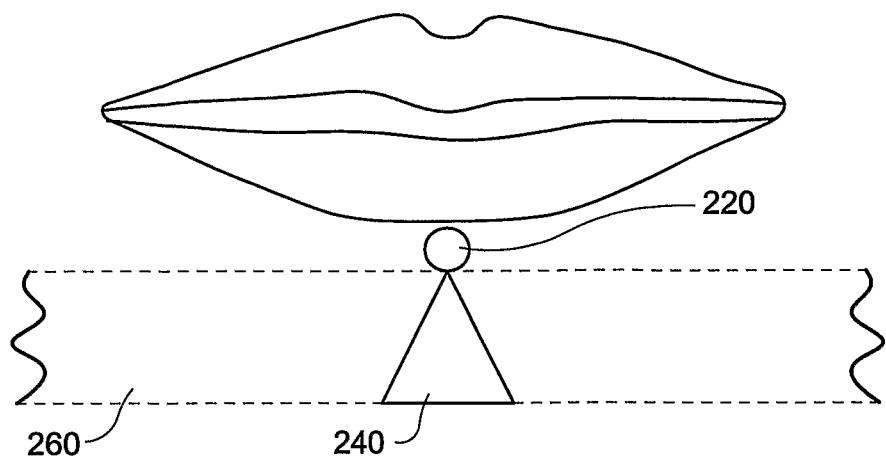
FIG. 2 is a schematic view of a mouth seal including a small ball according to an embodiment of the present technology.

In one form, the sealing portion may apply force only over a limited range, e.g., at a single point under the lower lip. For example, the single point force may be applied by an element such as, but not limited to, a small ball 220 as shown in FIG. 2. Such a small ball 220 may be held in place by any suitable means, for example, a supporting strap 260. Additionally, a support structure may be provided to the small ball 220 to secure it to the supporting strap 260, e.g., a member 240. The small ball and support structure may be made from any material that can provide some force to the lower lip, e.g., plastic, foam, gel, or silicone.

Figure 3:
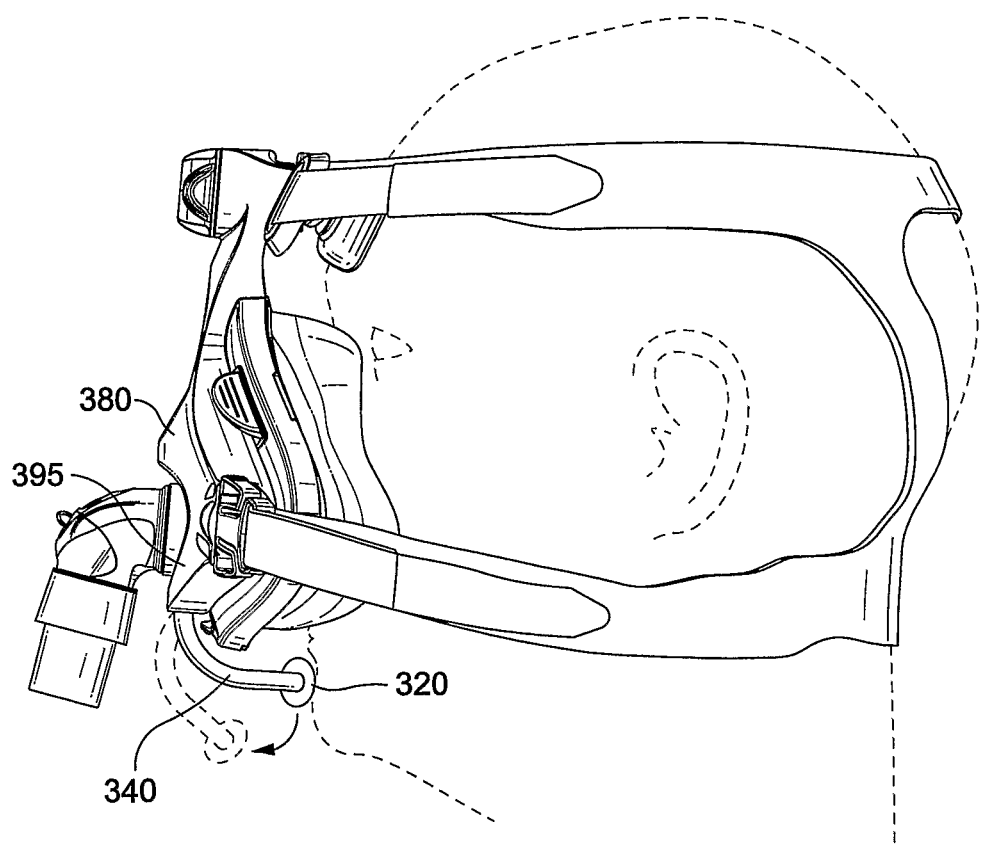
FIG. 3 is a side view of a mouth seal including a bar used in conjunction with a nasal mask according to an embodiment of the present technology.
Figure 4:
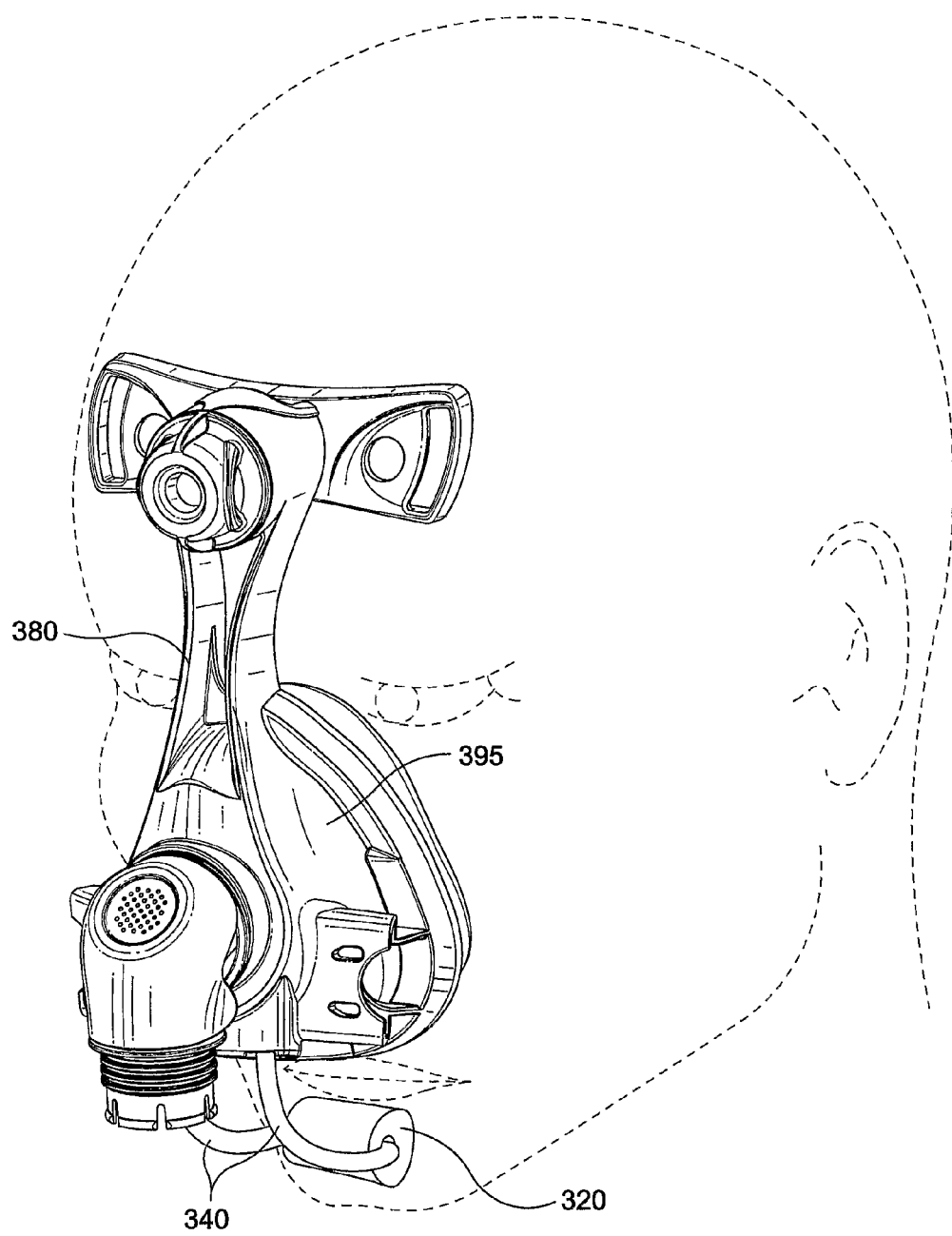
FIG. 4 is a perspective view of the mouth seal and nasal mask of FIG. 3.

In another form, the sealing portion may be in the form of a continuous element adapted to be provided below the lower lip to force the lower lip generally upwards. Such continuous element may be generally rigid, for example a cushioning mouth seal 320, e.g., made of or containing silicone, as shown in FIGS. 3 and 4. However, the mouth seal 320 may be constructed of a foam, gel or any other suitable material that may provide the generally upwards force and be comfortable for extended patient use. The mouth seal 320 may be slid, wrapped, co-molded or otherwise attached to support bars 340 (also referred to as bars) such that the mouth seal and bars are provided as a single piece. The bars 340 may be constructed from a malleable wire, TPE, rubber or any other generally flexible material such that the mouth seal may be adjusted as indicated by the arrow in FIG. 3. The single piece construction may be manufactured in high volumes by producing a continuous length of material 345 (i.e., a long piece of bar 340) with mouth seal 320 attached at equally spaced intervals, such that a single mouth seal may be cut off from a portion of the continuous length of material (see FIG. 4B).

Alternatively, the continuous element may be generally flexible, for example an elastic strap. The continuous element may be constructed from any suitable material, such as silicone, foam, gel, or a fabric such as BREATH-O-PRENE®.

1.1.3 Seal within Full-Face Breathing Cavity

In another embodiment, a full-face cushion may incorporate a mouth seal within the breathing cavity of the cushion, i.e., mouth seal integrated or part of the full-face cushion.

Figure 5:
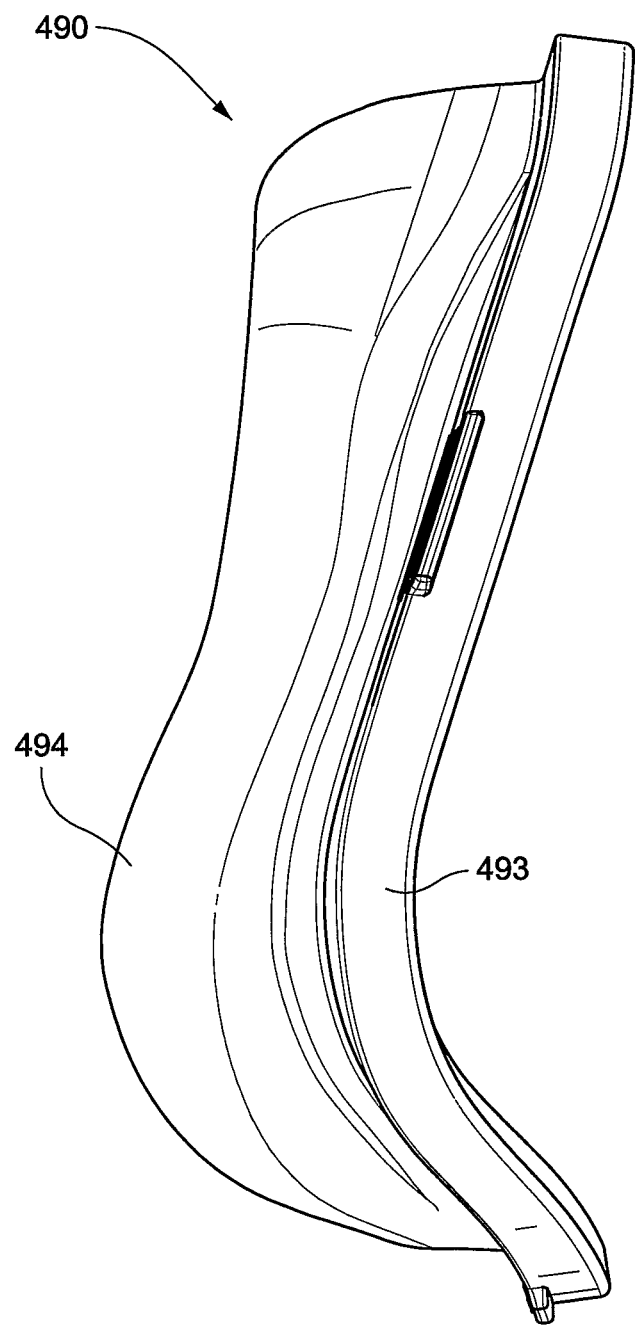
FIGS. 5 and 6 are side and front views of a full-face cushion incorporating a mouth seal according to an embodiment of the present technology.
Figure 6:
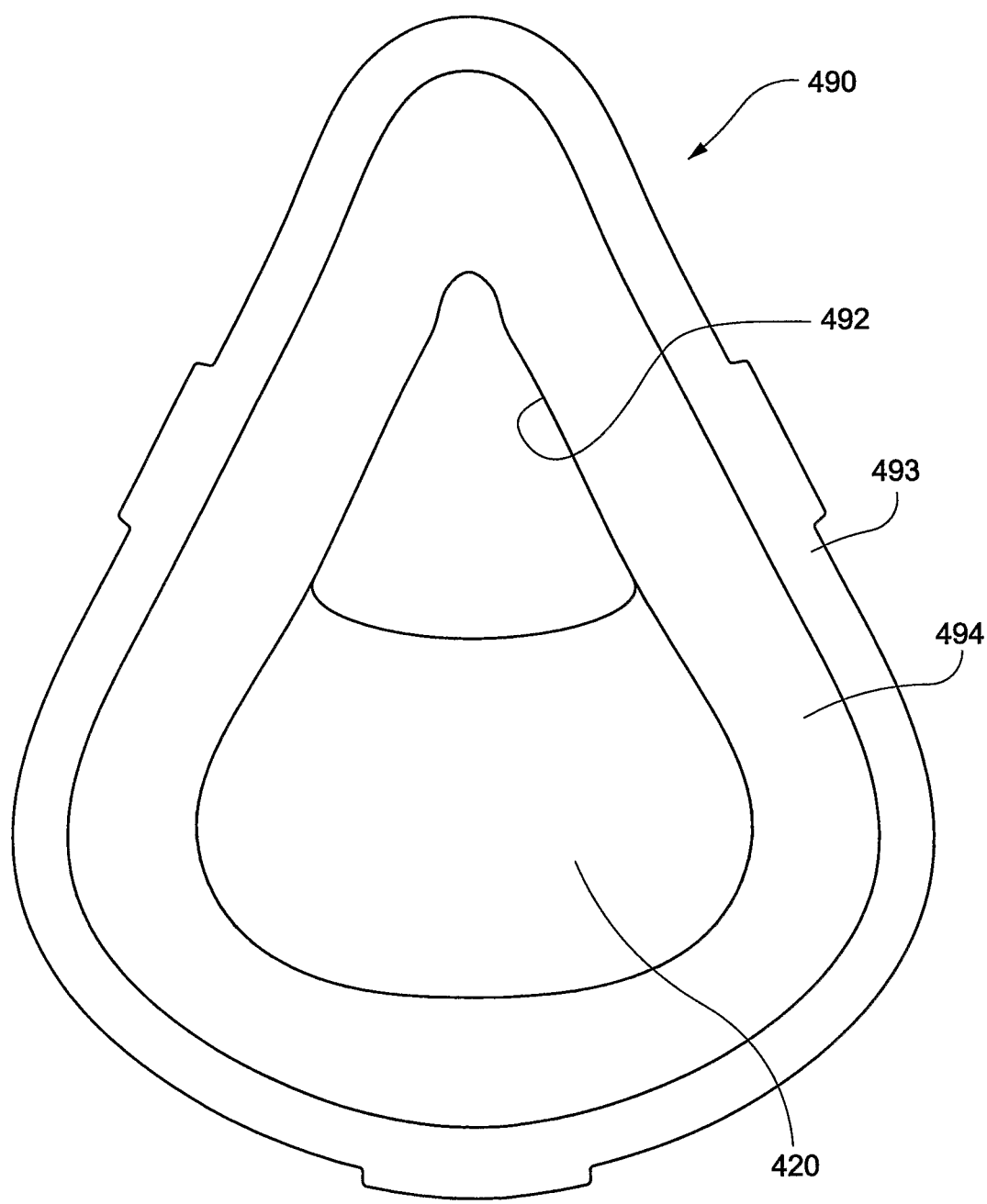

For example, FIGS. 5 and 6 illustrate a full-face cushion 490 including a base 493 and a membrane 494 extending from the base to provide a sealing structure. The membrane is adapted to form a continuous seal around the patient's nose and mouth and defines an aperture 492 to receive the patient's nose within a breathing cavity or chamber of the cushion.

The full-face cushion 490 also includes a thin flap 420 supported by the membrane 494, e.g., thin silicone flap, positioned and arranged to cover the breathing chamber adjacent the patient's mouth in use. In use, when the patient has a tendency for mouth leak, the pressure inside the patient's mouth pushes the patient's lips and/or cheeks against the thin flap 420, and the pressure inside the chamber creates a force pressing the flap 420 towards the patient's mouth. The action of the two opposing pressures forces the mouth seal against the patient's lips and prevents the patient from opening their mouth, i.e., combined action of the lips and/or cheeks inflating (due to pressure inside the patient's mouth) and the seal force against the lips (due to pressure inside the mask as delivered by the CPAP apparatus) prevents the patient from opening their mouth and breathing. Thus, the thin flap 420 prevents the patient's mouth from communicating with the breathing chamber while the aperture 492 allows communication with the air passages via the patient's nose only.

The patient may exhale onto the mouth seal portion or flap 420 if they exhale at a higher pressure than that inside the breathing chamber. The exhaled air preferably travels up into the breathing chamber via the aperture 492 at the patient's nose, rather than traveling downwards towards the patient's chin region and expelling into the atmosphere by breaking the seal of the cushion with the patient's face. This may be achieved by increasing the compliance of the flap 420 nearer the aperture 492 at the patient's nose and/or decreasing the compliance of the flap 420 at the patient's chin region. By exhaling through the mouth with the air expelling into the breathing chamber rather than atmosphere, treatment pressure is maintained. The pressure applied by the exhaled patient air is then released into the breathing chamber and/or equalized with the pressure in the breathing chamber, and the flap can then again prevent the patient's mouth from communicating with the breathing chamber. Once the pressure is released and/or equalized, the pressure inside the oral cavity of the user is relieved, which promotes nasal breathing as the mouth closes.

In an embodiment, such flap 420 may be part of a larger flap member typically molded with the full-face cushion. During an intermediate stage in the manufacturing process, the larger flap is removed to thereby form a nose and mouth aperture adjacent the breathing chamber that receives the patient's nose and mouth. Such larger flap is typically die cut in a secondary process to form the aperture. According to an embodiment of the present technology, the full-face cushion may be molded or manufactured in the same manner, but the larger flap is only partially removed to form aperture 492 while the lower portion of such larger flap is not removed thereby forming the mouth seal flap 420 which is dimensioned and arranged to be adjacent the patient's mouth in use.

In an alternative embodiment, such mouth seal flap could be a separate piece held by a strap and then the full-face mask worn over the mouth seal.

Figure 7:
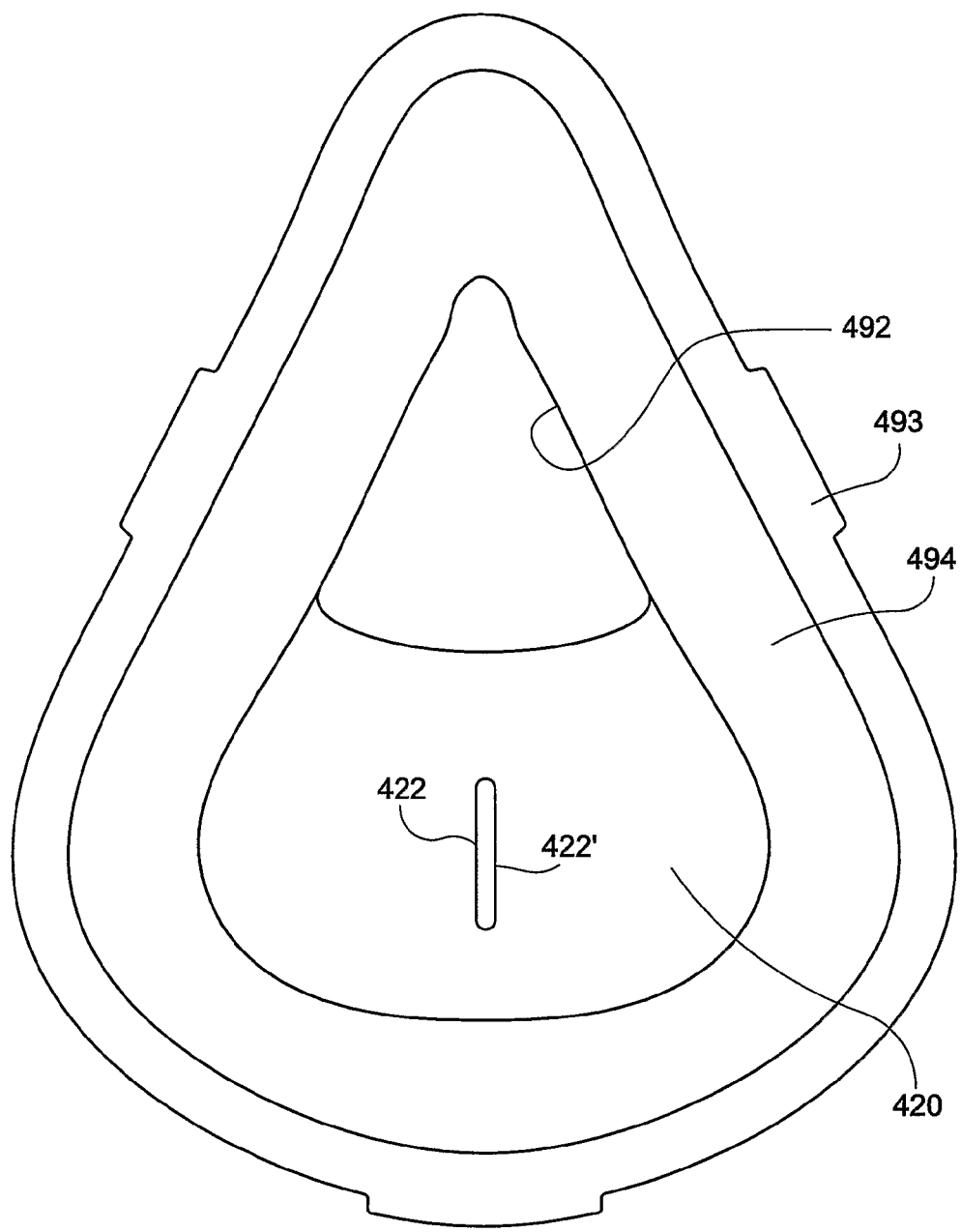
FIG. 7 is a front view of a full-face cushion incorporating a mouth seal according to another embodiment of the present technology.
Figure 8:
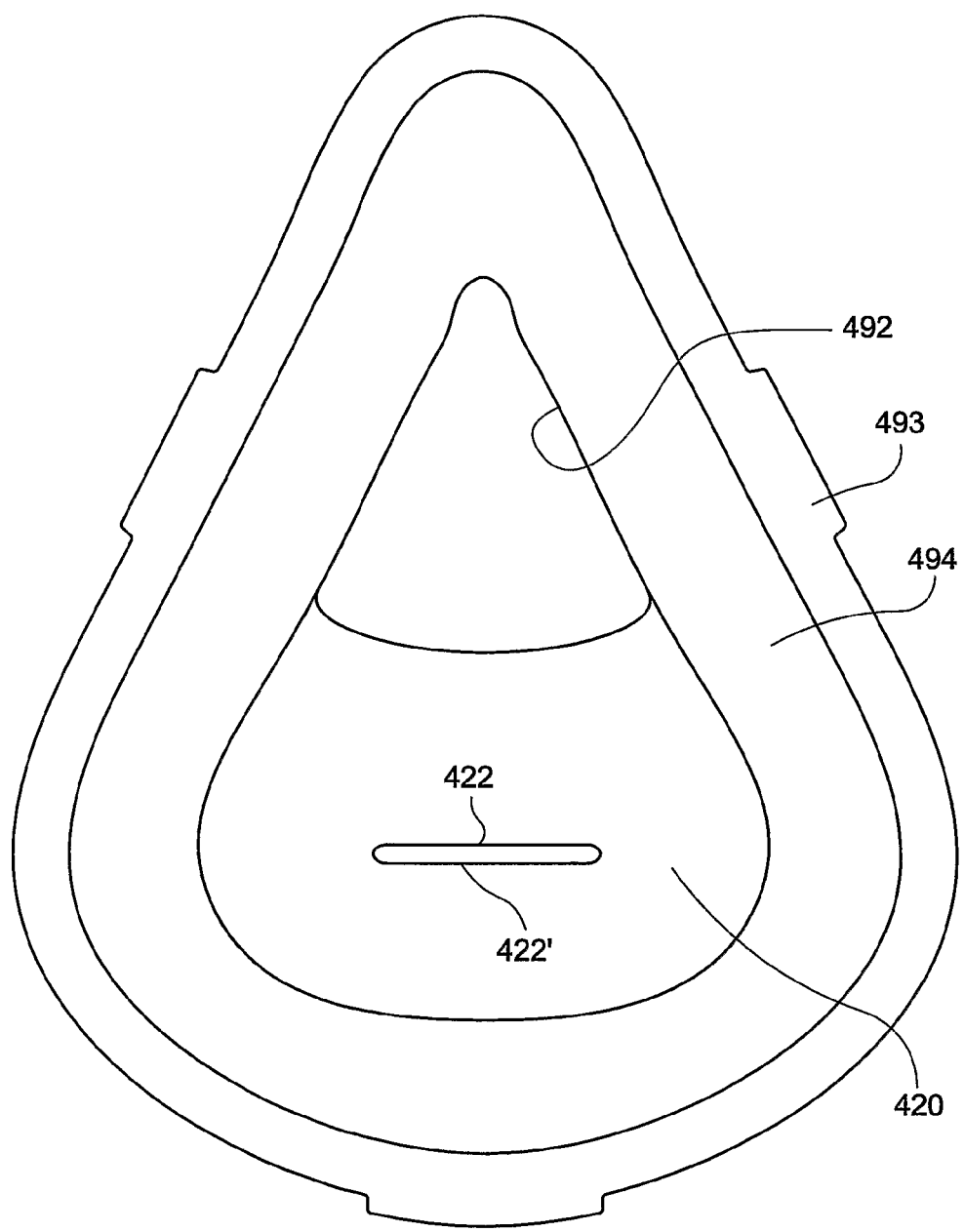
FIG. 8 is a front view of a full-face cushion incorporating a mouth seal according to another embodiment of the present technology.

In an embodiment, such flap 420 may include an elongated protrusion 422 to enhance the mouth seal in use. For example, the protrusion 422 may extend vertical and generally transverse to the patient's mouth to apply a force across both lips (see FIG. 7), or the protrusion 422 may extend horizontal and generally parallel to the patient's lips to apply a force to the patient's lower lip (see FIG. 8), e.g., in a manner as described above with respect to FIGS. 2 and 3.

Protrusion 422 may also be an aperture 422' so that the patient's mouth may communicate with the chamber if their nose were to unexpectedly block during the course of treatment.

It is noted that such full-face cushion allows the system to function with much lower force on the patient's face and lower jaw, e.g., due to sealed mouth and lower treatment pressures. Also, in an embodiment, a full-face mask including a cushion such as that shown in FIGS. 5-8 may be made smaller (i.e., have less height from the top of the patient's nose to below the patient's mouth) to allow the patient to open their mouth and breath in air from the atmosphere if the CPAP apparatus fails. This arrangement may replace the need for an anti-asphyxia valve.

In an alternative embodiment, the full-face cushion may include an anti-asphyxia valve (e.g., such as the anti-asphyxia valve disclosed in U.S. patent application Ser. No. 12/083,349, filed Apr. 10, 2008, which is incorporated herein by reference in its entirety) to allow inhalation in the event of CPAP failure. For example, the anti-asphyxia valve may be located in the mask elbow, along the side wall of the cushion, on the frame on which the cushion is supported, etc.

Figure 14:
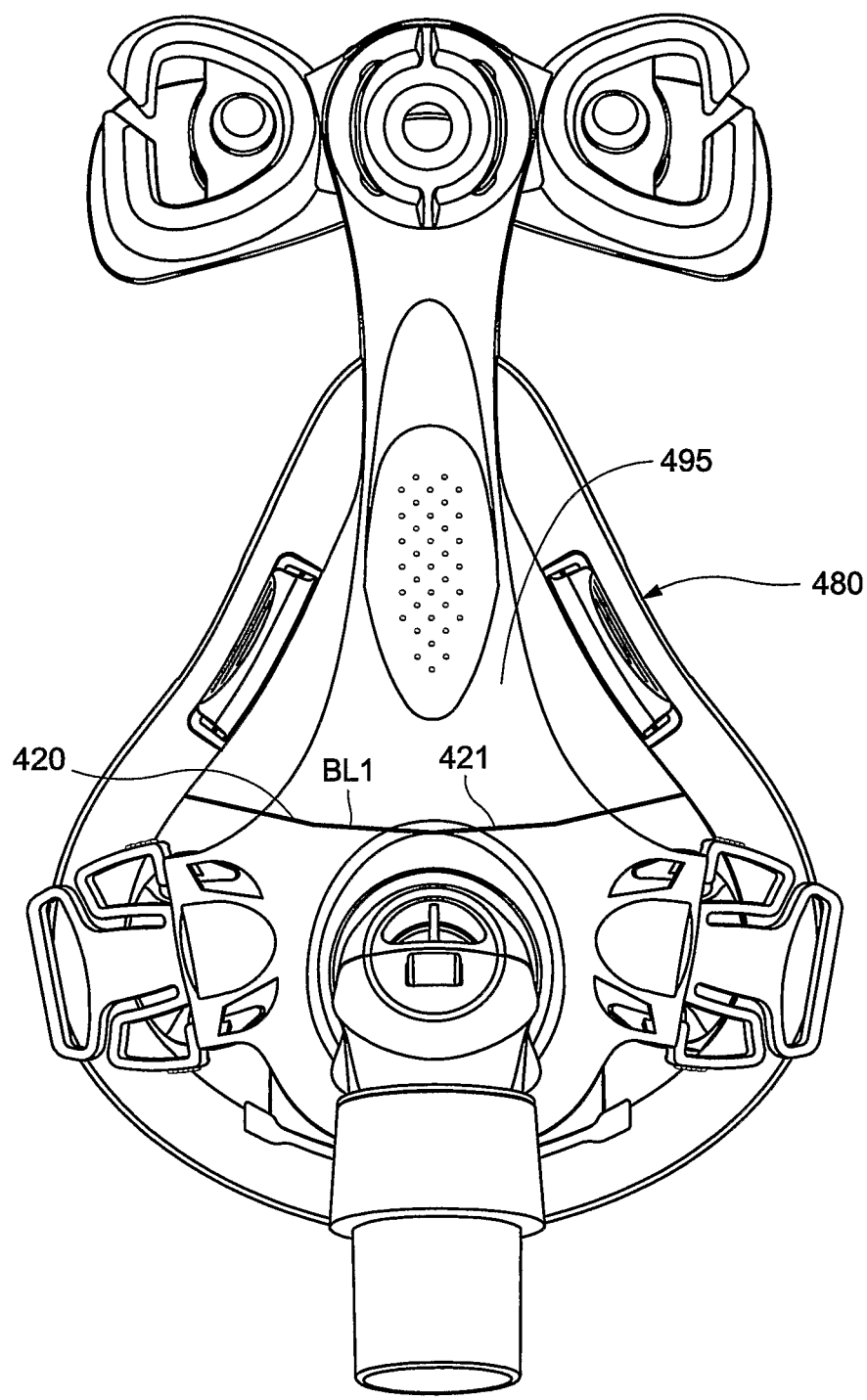
FIGS. 14, 15, and 16 are schematic front, side, and bottom views of a mouth seal used in conjunction with a full-face mask according to another embodiment of the present technology.
Figure 15:
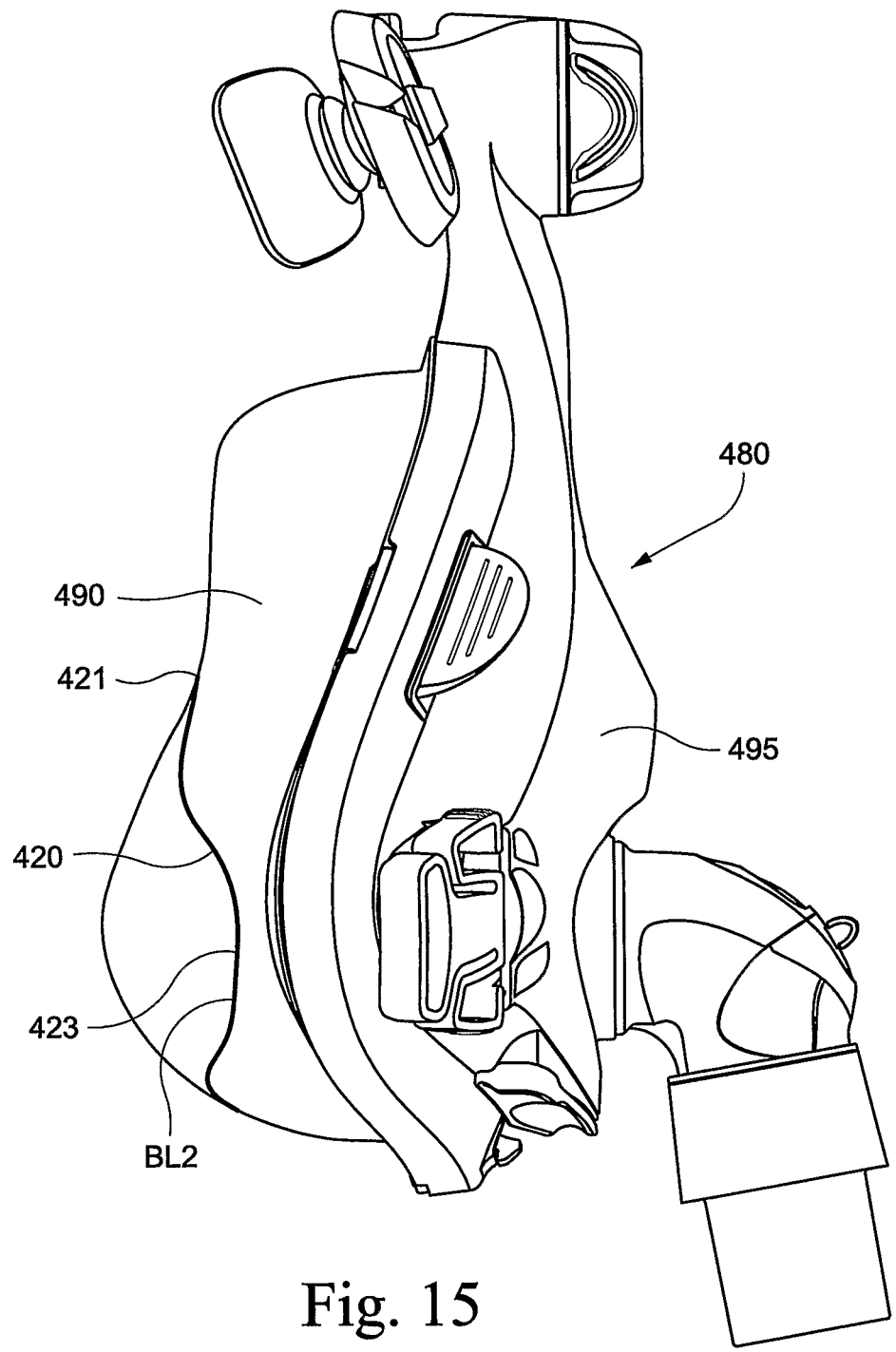
Figure 16:
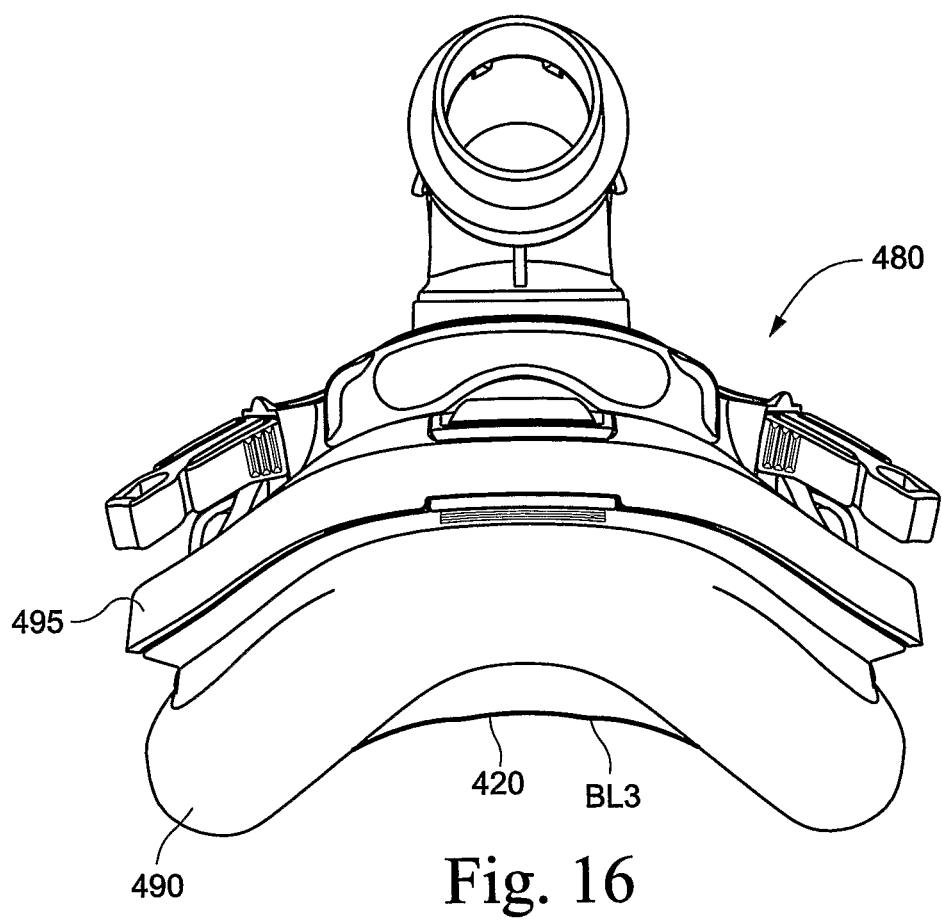

FIGS. 14-16 illustrate another example of such a full-face cushion 490 with a mouth seal flap provided to a full-face mask 480 including mask frame 495. A proposed edge of the thin flap 420 within the cushion 490 is indicated by a bold line BL1, BL2, BL3 in each view. For example, the bold line BL1 in FIG. 14 illustrates an upper edge 421 of the thin flap 420 which defines a part of the aperture 492 (e.g., see FIGS. 6-8) to receive the patient's nose, the bold line BL2 in FIG. 15 illustrates an exemplary contour of the thin flap 420 along its length, and the bold line BL3 in FIG. 16 illustrates an exemplary contour of the thin flap 420 along its width. The thin flap 420 may be formed as a flat piece or molded in a shape to generally conform to the patient's lips/mouth, e.g., see contoured portion 423 in FIG. 15. Moreover, contoured portion 423 of the thin flap may form a (sub-)chamber within the breathing chamber, which (sub-)chamber is at least partially or preferably completely isolated from the pressurized gas of the breathing chamber.

The illustrated full-face cushion and full-face mask is commercially sold under the name of MIRAGE QUATTRO™ by ResMed Limited. Further details and embodiments of such full-face mask are disclosed in U.S. patent application Ser. No. 11/793,055, filed Jun. 15, 2007, which is incorporated herein by reference in its entirety. However, it should be appreciated that the mouth seal may be used in conjunction with other suitable full-face masks, e.g., ResMed's MIRAGE LIBERTY™ mask.

Figure 17:
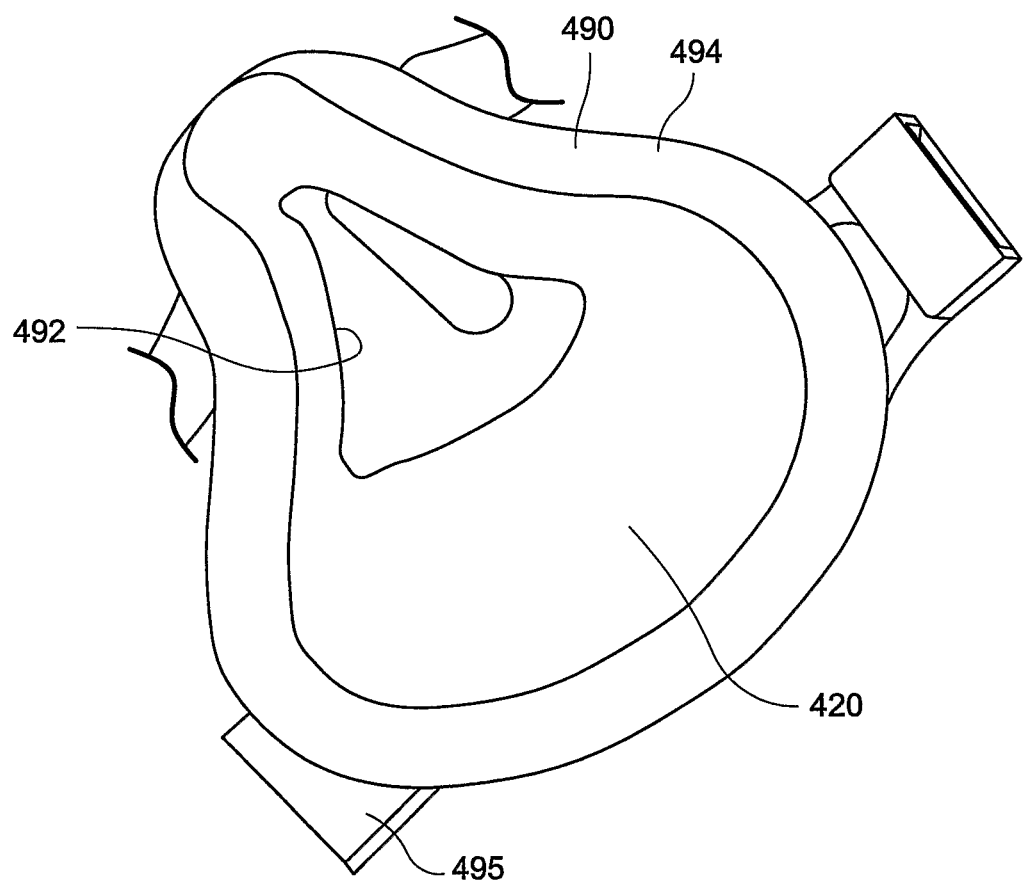
FIG. 17 is a perspective view of a full-face mask including a mouth seal according to an embodiment of the present technology.

FIG. 17 illustrates another example of a full-face cushion 490 with a mouth seal flap 420 provided to a mask frame 495. As illustrated, the cushion 490 provides a membrane 494 adapted to form a continuous seal around the patient's nose and mouth and defines an aperture 492 to receive the patient's nose.

In alternative embodiments, a mouth seal such as those shown in FIGS. 1-4 and 9-13 may be incorporated into the breathing cavity of the full-face cushion to lessen the sealing force requirement to the patient's face or lower jaw. In such embodiments, the mouth seal may be communicated with the breathing cavity of the full-face cushion, e.g., via a one-way valve or possibly allow free communication between the mouth seal and cushion as described in PCT Publication No. WO 2005/063378, published Jul. 14, 2005, which is incorporated herein by reference in its entirety.

1.1.4 Flexible Strip of Material

In another embodiment, the sealing portion of the mouth seal may include a silicone-filled, inflated, gel-filled, or foam-filled strip or cylinder structured to interface with the patient's mouth, and causing the mouth to seal against the sealing portion by inflation of the patient's cheeks and lips onto the sealing portion.

Figure 18:
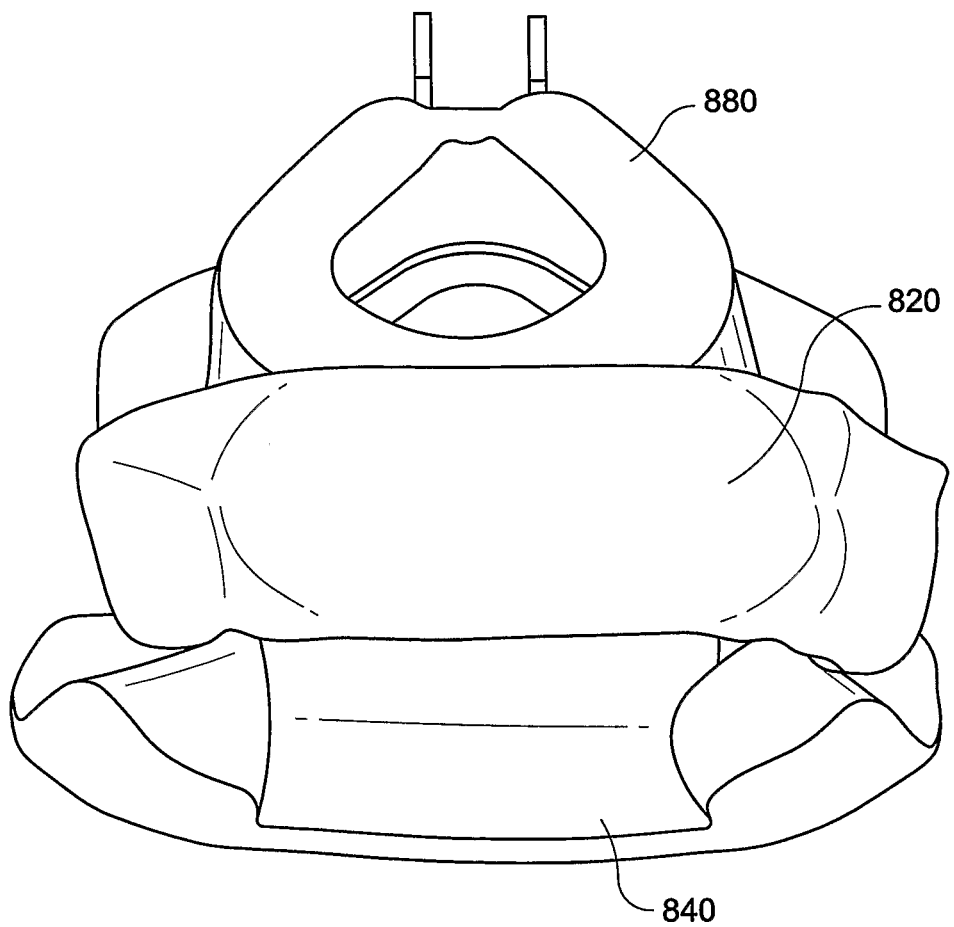
FIG. 18 is a perspective view of a mouth seal used in conjunction with a nasal mask according to another embodiment of the present technology.
Figure 19:
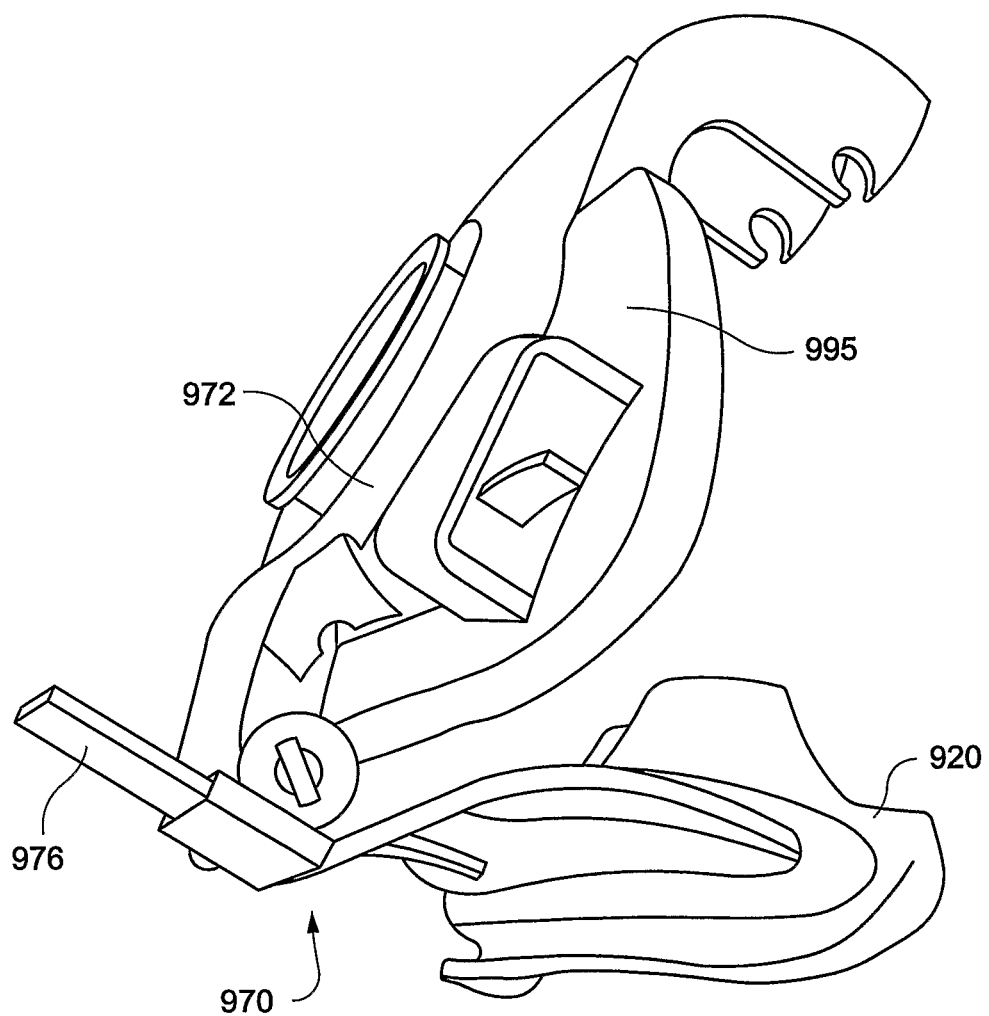
FIGS. 19, 20, 21, and 22 are perspective, side, front, and rear views of a mouth seal supported on a mask frame by a rack and pinion gear arrangement according to an embodiment of the present technology.
Figure 20:
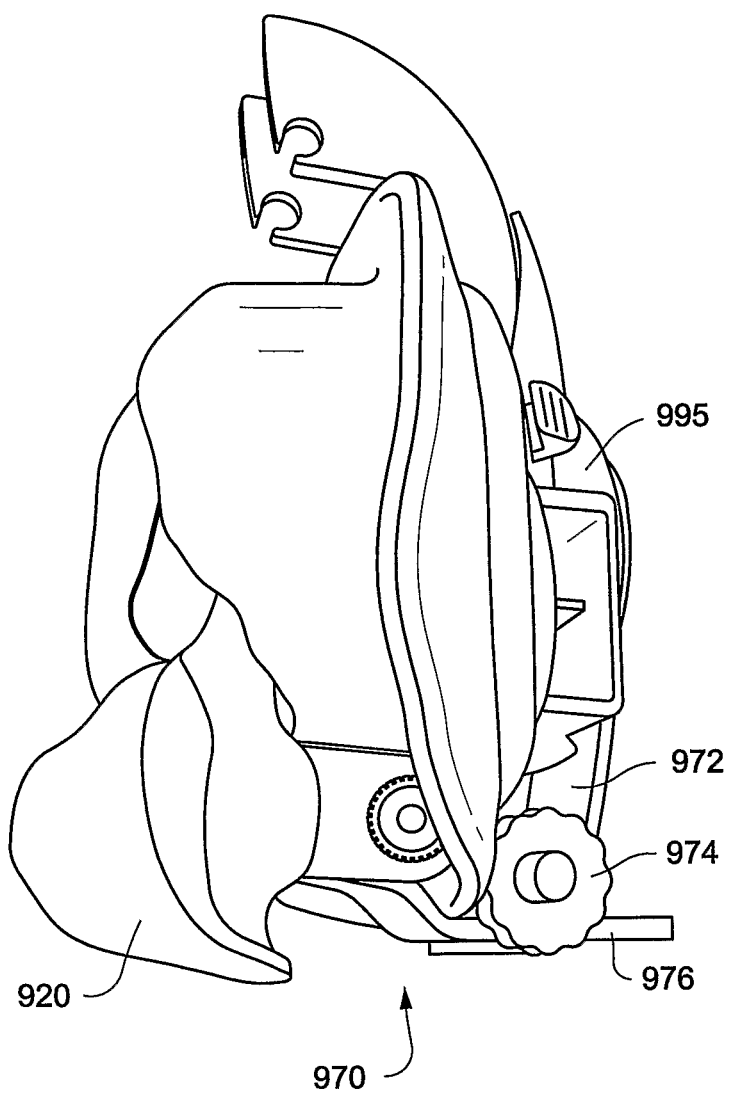
Figure 21:
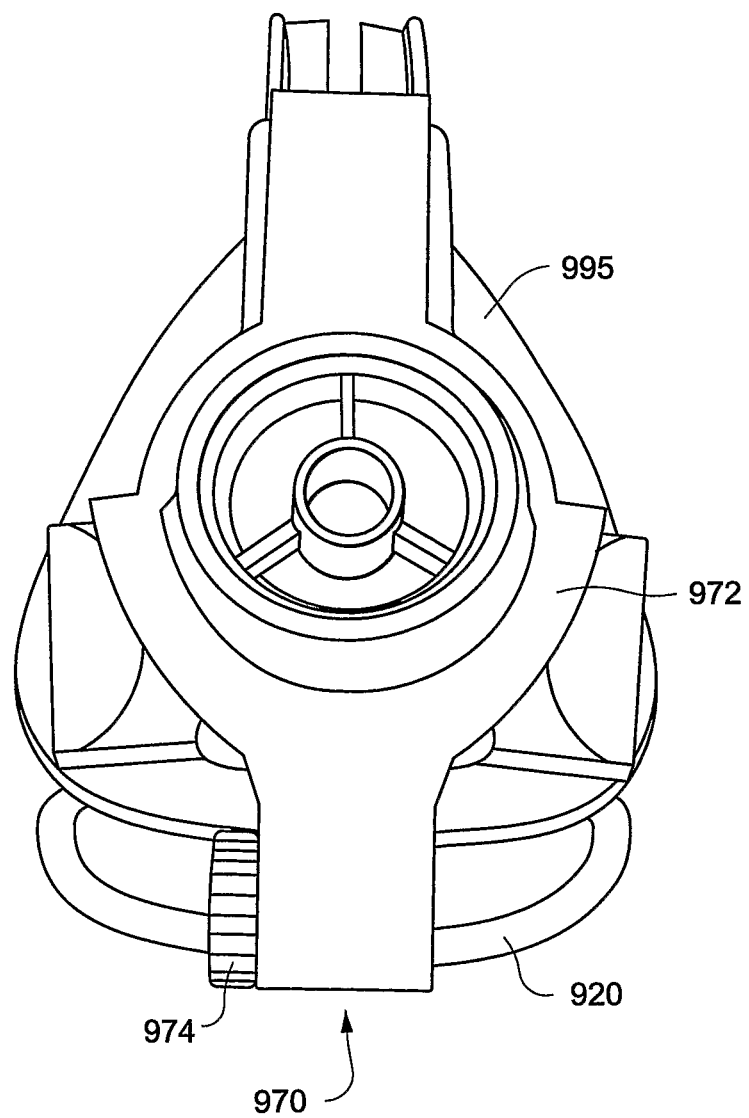
Figure 22:
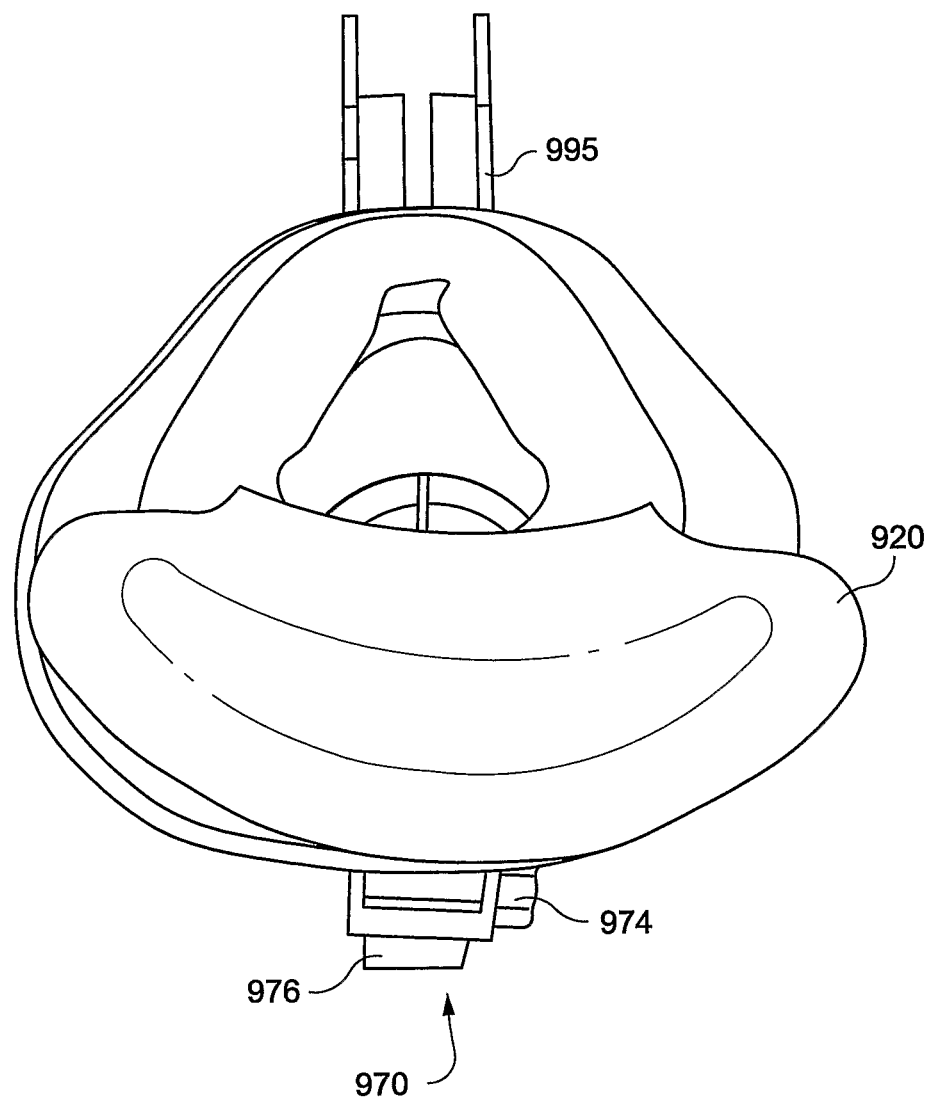

For example, FIG. 18 illustrates a silicone-filled, inflated, gel-filled, or foam-filled cylinder 820 used in conjunction with a nasal mask 880. As illustrated, a brace or other support structure 840 is provided between the cylinder 820 and the mask frame of the nasal mask to support the cylinder 820 on the nasal mask.

Figure 9:
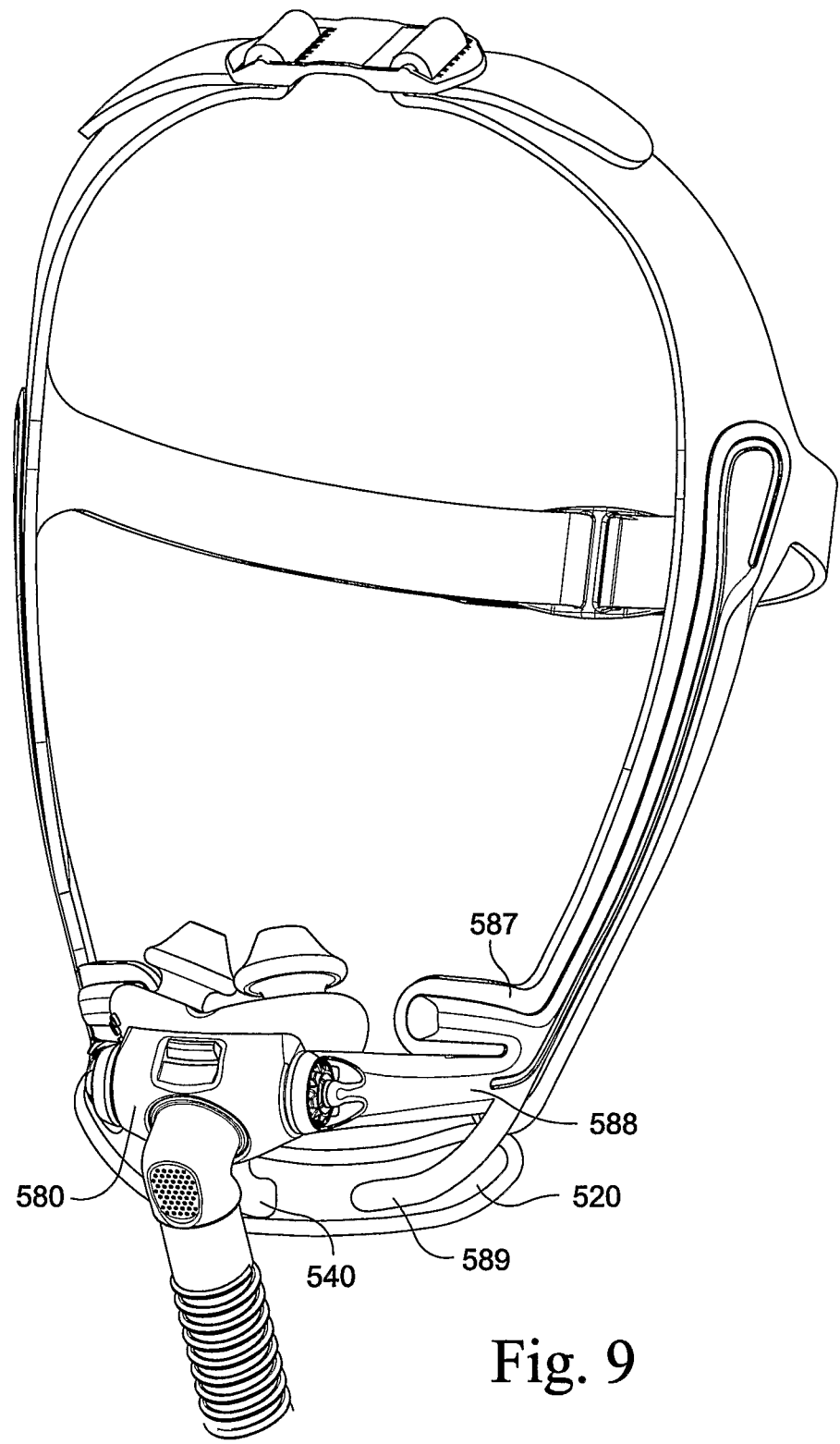
FIG. 9 is a perspective view of a mouth seal used in conjunction with a nozzle assembly according to an embodiment of the present technology.
Figure 10:
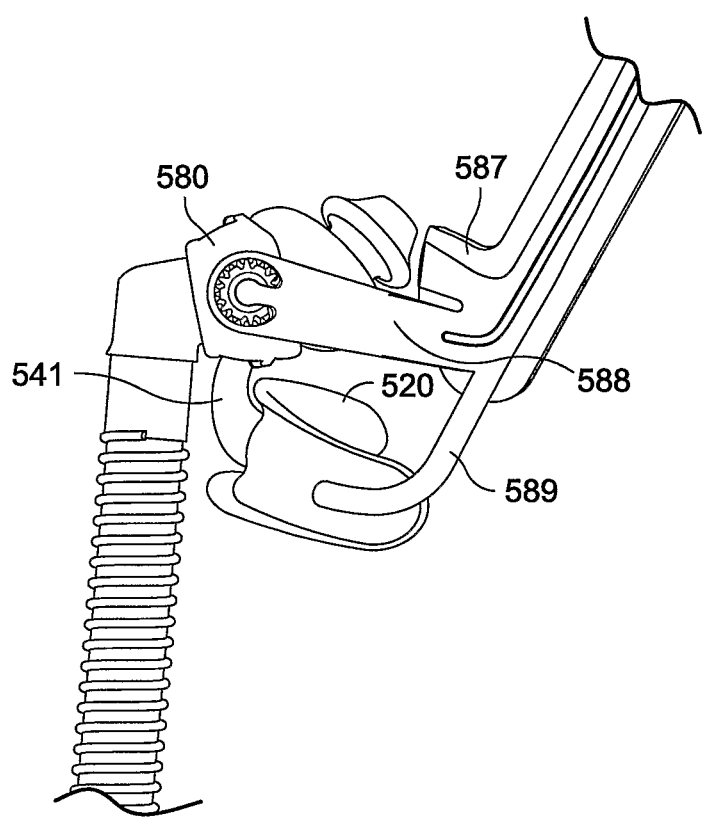
FIG. 10 is a side view of the mouth seal and nozzle assembly of FIG. 9.

FIGS. 9 and 10 illustrate another example of a mouth seal in the form of a substantially flat strip of silicone 520 or similar flexible material including a length and height sufficient to completely cover the patient's mouth. A small groove may be incorporated into the strip to assist locating the patient's lips to the mouth seal. In addition, the strip 520 is curved to generally conform to the curvature of the patient's mouth region. Alternatively, the strip 520 may be constructed of a conformable material such as a malleable wire, a thermoformable material, or any other suitable material, such that the patient can deform the strip 520 to align with their mouth in use.

In an embodiment, such mouth seal may be relatively narrow, e.g., for patients whose mouth does not fall open when asleep. The narrow mouth seal may allow the patient to open their mouth when not in use, e.g., to talk. This approach may be particularly advantageous for use with a nozzle assembly such as that shown in FIGS. 9 and 10.

In this embodiment, the mouth seal may be used without the anti-asphyxia valve as the patient may open his/her mouth to breath when air pressure is not present, e.g., in the case CPAP failure. This is possible since a seal is formed by air pressure causing the patient's lips to "bellow". Thus, the seal is only "activated" when air pressure is present.

Additional embodiments of such mouth seals are disclosed in U.S. patent application Ser. No. 11/988,931, filed Jan. 17, 2008, which is incorporated herein by reference in its entirety.

1.2 Support Structure

The mouth seal may include a support structure to support the sealing portion in place adjacent the patient's mouth. Such support structure may include a mount structured to mechanically support the mouth seal on the mask system and/or a strap arrangement. In an embodiment, the mouth seal may be an integral part of the mask cushion.

1.2.1 Mounted to Mask System with Airway Communication

The mouth seal 10 of FIG. 1 is structured to be used in conjunction with a nasal interface 80 (including nasal and full-face masks, pillows, nozzles, nasal pillows or prongs, etc.) that provides pressurized breathable gas to the patient's nose. As illustrated, a mount in the form of a conduit portion 40 interconnects the sealing portion 20 with the nasal interface 80. The conduit portion 40 communicates with an opening 82 provided to the nasal interface 80. A mechanism, e.g., a one-way valve 85 or a simple flap or similar component, etc., is provided to the opening 82 to define a one-way air path that allows exhalation gas from the chamber 25 to enter and exhaust through the breathing cavity or chamber of the nasal interface 80, but prevents pressurized gas in the nasal interface 80 from entering the mouth seal 10. Thus, the mouth seal 10 is isolated from the supply of pressurized air provided to the nasal interface 80, but exhalation gas from the patient's mouth may be exhausted into the nasal interface 80 when mouth pressure (pressure within cavity 25 of mouth seal 10) exceeds mask pressure (pressure within breathing cavity of nasal interface 80). If the CPAP machine fails, the patient can breathe in through the mouth seal 20 (e.g., via anti-asphyxia valve 50) and out through the nasal interface 80 and the inlet tube 84 back to the CPAP machine at or close to atmospheric pressure.

The patient's lips and/or cheeks may protrude into sealing contact with the mouth seal 10 due to increased pressure in the patient's oral cavity. If the patient exhales through the patient's mouth, pressure may build up in the seal cavity 25 and in the conduit portion 40. When the pressure in the mouth seal cavity 25 and the conduit portion 40 exceeds the pressure in the interface 80, the one-way valve 85 is opened and the excess pressure in the mouth seal cavity 25 and the conduit portion 40 is released. The pressure in the mouth seal cavity 25 and the conduit portion 40 may be equalized with the pressure in interface 80. Once the pressure in the mouth seal cavity 25 and the conduit portion 40 is released and/or equalized with the pressure in the interface 80, nasal breathing may be promoted as the mouth closes.

Alternatively, the one-way valve 85 may only open when the pressure in the mouth seal cavity 25 and the conduit portion 40 exceeds the pressure in the interface 80 by a predetermined threshold. Valve 85 may be biased to at least in part define the threshold, or alternatively no bias in the valve 85 may be used. If biased, the valve 85 is likely biased in a closed position, although it is possible to bias the valve 85 in an open position-relying on pressurized gas in the interface 80 to close the valve 85.

In embodiments, the conduit portion 40 can connect to one or more mask ports, e.g., as the support bars 340 are connected to the ports in FIG. 4. Such mask ports are more fully described and shown in U.S. Pat. No. 7,669,599, which is incorporated herein in its entirety. When the conduit portion 40 is connected to the one or more mask ports, the oneway valve 85 may be located within the conduit portion 40, somewhere between its ends. Ports can be used to support a variety of accessories, some being pneumatic in nature.

In this embodiment, the patient is encouraged to breathe through their nose. Moreover, this system thus provides the treatment benefits of a full-face mask without the disadvantages associated with encouraging mouth breathing with potentially higher AHI or applying backward pressure to the lower jaw.

In an alternative, the pressure in the mouth seal 10 may be released and/or equalized with the atmosphere, instead of being released and/or equalized with the interface 80. In such embodiments, a mechanism such as a one-way valve or equivalent may be provided on the mouth seal 10, and open to the atmosphere. Further, such embodiments may be provided without the conduit 40, so that there is no communication between the mouth seal 10 and the interface 80, and pressure built up in the mouth seal 10 is released and/or equalized to the atmosphere.

1.2.2 Mounted to Mask System without Airway Communication

In an alternative embodiment, the mouth seal may be mounted to the mask system without any airway communication. For example, the mouth seal may include a mount structured to attach to the mask frame, ports, and/or headgear connectors/receptacles.

For example, FIGS. 3 and 4 illustrate mouth seal 320 coupled to a nasal mask 380 via spaced apart support bars 340. The bars 340 may be mechanically mounted to the mask frame 395 or the bars 340 may be adapted to mechanically engage respective ports provided to the lower end of the mask frame 395.

The illustrated nasal mask 380 is commercially sold under the name of MIRAGE MICRO™ by ResMed Limited. However, it should be appreciated that the mouth seal may be used in conjunction with other suitable nasal masks and mask types, e.g., nozzles or nozzle assembly, nasal prongs, full-face mask, etc.

In an embodiment, the position of the mouth seal with respect to the mask system may be adjusted, i.e., so as to adjust the position of the mouth seal with respect to the patient's mouth. For example, the position of the mouth seal in the anterior-posterior plane (i.e., generally in the direction of the back of the patient's head to the front of the patient's head) may be altered by an adjuster, e.g., a ratchet system or a spring, as indicated by the arrow and shown in dashed lines in FIG. 3. In an embodiment, an over-center spring system may be used that allows the mouth seal to be lifted away when not in use, e.g., for speaking.

FIGS. 19-22 illustrate an embodiment in which the mouth seal 920 is supported on the mask frame 995 by a rack and pinion gear arrangement 970. As illustrated, the arrangement 970 includes a base having an upper portion 972 provided to the frame 995 (e.g., via a mechanical interlock, adhesive, etc.) and a lower portion that supports an adjustable dial 974 with a circular pinion. A flat bar or rack 976 including a series of teeth is provided to the mouth seal 920. The flat bar 976 is engaged with the pinion of the dial 974 such that rotational motion of the dial 974 will cause the rack 976 and hence the mouth seal 920 to move towards and away from the patient's mouth.

It should be appreciated that the adjustable mounting of the mouth seal with respect to the mask may be applied to mask systems with and without airway communication via the one-way valve with the nasal interface.

1.2.3 Mounted to Headgear

In an alternative embodiment, the mouth seal may be supported by headgear adapted to support the mask system on the patient's head in use.

For example, FIGS. 9 and 10 illustrate the mouth seal 520 used in conjunction with a nozzle assembly 580. As illustrated, the nozzle assembly 580 includes headgear 586 including side straps 587 (e.g., constructed of BREATH-O-PRENE®) and rigidizers or headgear yoke 588 (e.g., constructed of a molded plastic such as nylon) attached to the side straps 587.

The illustrated nozzle assembly 580 is commercially sold under the name of SWIFT™ LT by ResMed Limited. Further details and embodiments of such nozzle assembly are disclosed in U.S. patent application Ser. No. 12/219,852, filed Jul. 29, 2008, which is incorporated herein by reference in its entirety. However, it should be appreciated that the mouth seal may be used in conjunction with other suitable nozzle assemblies and mask types, e.g., nasal mask, full-face mask, etc.

According to an embodiment of the present technology, an extended portion 589 may be provided to each rigidizer 588 to retain a respective end of the mouth seal 520. The extended portion 589 may be integrally formed with the rigidizer 588 or formed separately and attached thereto (e.g., by clipping, hook and loop material, or any other suitable attachment means). In an alternative embodiment, a non-rigid component may be used to retain the mouth seal, e.g., strap material provided to or formed as part of headgear.

As shown in FIG. 9, an anti-asphyxia valve 540 may be provided to the mouth seal 520 to provide an air passage to the patient in the absence of pressure. In an embodiment, as shown in FIG. 10, a conduit 541 may be provided that is adapted to communicate the mouth seal with the breathing cavity of the nozzle assembly, e.g., in a manner described above with respect to FIG. 1. The conduit 541 may include a one-way valve (not shown), such as the one-way valve 85 illustrated in FIG. 1, to define a one-way air-path that allows exhalation gas exhaled by the patient to mouth seal 520 to enter and exhaust through the breathing cavity of the nozzle assembly 580, but prevents pressurized gas from the nozzle assembly 580 from entering the one-way valve and the mouth seal 520.

If the CPAP machine fails, the patient can breathe in through the mouth seal 520 (e.g., via anti-asphyxia valve 540) and out through the nozzle assembly 580 and the inlet tube back to the CPAP machine at or close to atmospheric pressure.

In this embodiment, the mouth seal 520 may be used as a physical support for supporting the nozzle assembly 580 on the patient's face in use, e.g., which may allow elimination of one or more components from the nozzle assembly (e.g., eliminate cheek and/or frame supports from headgear).

In an alternative embodiment, the mouth seal 520 may be retrofit to a nozzle assembly using a clip-on type mount adapted to clip the mouth seal to the nozzle assembly, e.g., clips to frame. In such mouth seal arrangement, the mouth seal may include no valves (e.g., no one-way valve communicated with breathing cavity) or an anti-asphyxia valve only.

1.2.4 Integral with Mask Cushion

In another embodiment, the mouth seal may be integrated with the mouth cushion, e.g., mechanically attached or integrally formed in one piece therewith.

For example, as described above, FIGS. 5-8 and 14-16 illustrate an embodiment in which a full-face cushion 490 includes an integrated mouth seal 420 via a partially cut aperture.

FIGS. 11, 11B, 12, 12B, and 13 illustrate embodiments in which the mouth seal 620, 720 extends downwardly from the lower end of a nasal cushion 681 of a nasal mask 680. In such embodiment, the mouth seal 620, 720 may be integrally formed with the nasal cushion 681 or formed separately and mechanically attached thereto, e.g., via an adhesive.

The illustrated nasal mask 680 is commercially sold under the name of MIRAGE ACTIVA™ by ResMed Limited. Further details and embodiments of such nasal mask are disclosed in U.S. Patent Publication No. 2004-0118406, published Jun. 24, 2004, which is incorporated herein by reference in its entirety. However, it should be appreciated that the mouth seal may be used in conjunction with other suitable nasal masks (e.g., ResMed's ULTRA MIRAGE™ II mask) and mask types, e.g., nozzles, nasal prongs, full-face mask, etc.

In an embodiment, the nasal cushion 681 and mouth seal 620 merge along a contact strip 627 positioned along the patient's top lip in use as shown in FIG. 11. Such contact strip 627 may form a "duck-bill" like valve which allows exhalation from the patient's mouth to be exhausted into the nasal cushion 681 when mouth pressure (pressure in the mouth seal) exceeds mask pressure (pressure in the nasal mask).

In an embodiment, the nasal cushion 681 may involve an extension 683 (as indicated in dashed lines) to balance the force requirements of the mouth seal as shown in FIG. 11. That is, the lower end of the nasal cushion (e.g., gusset portion and/or face-contacting portion of the cushion) may be elongated or extended in length to increase the contact force applied to the patient's face for use with the mouth seal.

In an embodiment, a brace or other support structure 640 (as shown in FIG. 12B and schematically indicated in dashed lines in FIG. 12) may be provided between the mouth seal and the mask frame to further support the mouth seal on the nasal mask.

Also, similar to the embodiment described above, the mouth seal 620 of FIGS. 11 and 11B and the mouth seal 720 of FIGS. 12, 12B, and 13 may provide communication with the breathing cavity of the respective nasal cushion, e.g., via a one-way valve provided to the mouth seal 620, 720, providing one-way communication of exhalation gases from the mouth seal 620, 720 to the breathing cavity of the respective nasal cushion 681.

1.2.5 Strap Arrangement

The mouth seal may be held against the patient's lips by a strap arrangement which includes a strap that extends around the back of the patient's neck. Ends of the strap may be attached to the mouth seal in any suitable manner, e.g., anchors, hook and loop fasteners, etc. Thus, the mouth seal may not be attached to the mask system or headgear, and held in place by encompassing the head of the patient. However, such strap arrangement may be used in conjunction with mask or cushion mounts as described above.

For example, FIG. 2 illustrates the mouth seal including a small ball 220 held in place by a supporting strap 260.

1.3 Anti-Asphyxia Valve

The mouth seal may include an anti-asphyxia valve that provides an air passage to the patient in the absence of pressure. The anti-asphyxia valve is provided to the mouth seal to allow the patient to breathe in freely in the absence of pressure (e.g., PAP device fails, power supply failure, etc.) but prevent exhalation. In use, the mouth pressure must be less than atmospheric pressure to allow air into the cavity of the mouth seal. For example, FIGS. 1 and 11 illustrate mouth seals 20, 620 with respective anti-asphyxia valves 50, 650.

In an alternative embodiment, the mouth seal may be used without an anti-asphyxia valve. In this embodiment, the patient may open his/her mouth to breath when air pressure is not present. This may be possible since a seal is formed by air pressure causing the patient's lips to "bellow". Thus, the seal is only "activated" when air pressure is present. In addition, the mouth seal may be relatively narrow to allow the patient to open his/her mouth to breath.

1.4 Alternative Arrangements

As noted above, nasal breathing may be preferable to reduce AHI and/or CPAP treatment pressures. To enhance nasal breathing and/or ensure clear nasal airways, nasal dilators (e.g., nasal dilator such as that disclosed in U.S. patent application Ser. No. 11/886,677, filed Sep. 19, 2007, which is incorporated herein by reference in its entirety) and/or nasal insufflation (TNI) type technology (e.g., using a nasal cannula to deliver warm, humidified air at a high flow rate such as that disclosed in U.S. Provisional Patent Application Nos. 61/058,659, filed Jun. 4, 2008, and 61/080,847, filed Jul. 15, 2008, each of which is incorporated herein by reference in its entirety) may be integrated into mask systems. For example, a nasal dilation device may be integrated into a mask system that is structured to engage the patient's nose so as to maintain open nasal passageways.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A mask system, comprising:
   an interface adapted to deliver pressurized gas to a patient's nasal airways;
   a mouth seal adapted to seal with the patient's mouth and to prevent inhalation through the mouth when pressure is supplied in the interface, wherein the mouth seal is adapted to be adjacent to or in light contact with the patient's mouth such that increased pressure in the patient's mouth causes the patient's lips and/or cheeks to seal with the mouth seal; and
   a one-way air path in air communication with the interface and with the mouth seal, wherein the one-way air path allows exhausted air from the mouth seal to pass into the interface, but prevents the pressurized gas from the interface from passing into the mouth seal.

2. The mask system according to claim 1, wherein the mouth seal includes a cavity adapted to receive the patient's mouth and a conduit portion that communicates the cavity with the interface.

3. The mask system according to claim 1, further comprising a one-way valve provided along the air path.

4. The mask system according to claim 1, wherein the mouth seal includes an anti-asphyxia valve structured to provide an air passage to the patient in the absence of the pressure in the interface.

5. The mask system according to claim 1, wherein the interface comprises a nasal mask.

6. The mask system according to claim 1, wherein the interface comprises a full-face mask.

7. The mask system according to claim 1, wherein the interface comprises a cushion adapted to form a seal around at least the patient's nose, and the mouth seal is formed in one piece with the cushion.

8. The mask system according to claim 1, wherein the interface comprises nozzles.

9. A mask system according to claim 1, wherein:
   the interface is a nozzle assembly including a pair of nozzles structured to sealingly communicate with nasal passages of the patient's nose; and
   further comprising headgear to maintain the nozzle assembly in a desired position on the patient's face, the headgear including side straps and rigidizers provided to respective side straps, and each rigidizer including an extended portion to retain a respective end of the mouth seal.

10. The mask system according to claim 9, wherein the extended portion is integrally formed with the respective rigidizer.

11. The mask system according to claim 9, further comprising a mount to interconnect an intermediate portion of the mouth seal with the interface.

12. The mask system according to claim 11, wherein the mount is communicated with the interface via the one-way air path.

13. The mask system according to claim 11, wherein the mount includes an anti-asphyxia valve structured to provide an air passage to the patient in the absence of the pressure.

14. The mask system according to claim 1,
   wherein the interface comprises a cushion adapted to form a seal around at least the patient's nose;
   wherein the mouth seal is formed in one piece with the cushion.

15. The mask system according to claim 14, wherein the cushion is a nasal cushion and the mouth seal extends from a lower end of the nasal cushion.

16. The mask system according to claim 1, further comprising:
   an adjustment mechanism structured to adjust a position of the mouth seal with respect to the interface.

17. The mask system according to claim 16, wherein the adjustment mechanism includes a rack and pinion gear arrangement.

18. The mask system according to claim 17, wherein the rack and pinion gear arrangement includes a dial that allows selective adjustment of the mouth seal.

19. The mask system according to claim 1, wherein the mouth seal is adapted to seal with the patient's mouth without applying excess rearward force to the patient's jaw.

20. The mask system according to claim 1, wherein the mouth seal is adapted to prevent inhalation of the pressurized gas through the mouth when the pressure is supplied in the interface.

21. The mask system according to claim 1, wherein the mouth seal is adapted to allow the patient to breath through the patient's mouth, around the mouth seal, when the pressure is not supplied in the interface.

22. The mask system according to claim 1, wherein the mouth seal is structured to be spaced apart from the patient's mouth in the absence of internal pressurization of the patient's mouth.

23. A method of controlling air flow in a mask system to reduce mouth breathing of a patient, the mask system having a nasal interface adapted to form an air interface to deliver pressurized gas to the patient's nose, a mouth seal adjacent to or in light contact with the patient's mouth and adapted to seal the patient's mouth, and an air conduit between the nasal interface and the mouth seal, the method comprising:
- increasing pressure in the patient's mouth to cause the patient's lips and/or cheeks to seal with the mouth seal;
- allowing air exhausted from the patient to the mouth seal to pass through the air conduit and into the nasal interface;
- preventing the pressurized gas from the air interface from passing into the mouth seal; and
- using the mouth seal to prevent the patient from inhaling through the patient's mouth in the presence of pressurized gas delivered to the nasal interface.

24. The method of claim 23, further comprising providing an air passage to the mouth seal in the absence of the pressurized gas delivered to the nasal interface.

25. The method of claim 24, wherein the air passage provided to the mouth seal is provided by an anti-asphyxia valve.

26. The method of claim 23, further comprising:
- delivering pressurized gas within the nasal interface; and
- equalizing pressure between the nasal interface and the mouth seal when the pressure in the mouth seal exceeds the pressure within the interface.

27. The method of claim 26, wherein the pressure between the nasal interface and the mouth seal is equalized when the pressure in the mouth seal exceeds the pressure within the interface by a predetermined threshold.

28. The method of claim 26, further comprising forming a seal between the user and the mouth seal when the user's lips and/or cheeks protrude into sealing contact with the mouth seal.

29. A mask system, comprising:
- an interface adapted to deliver pressurized gas to a patient's nasal airways, the interface comprising a cushion adapted to form a seal around at least the patient's nose;
- a mouth seal adapted to seal with the patient's mouth and to prevent inhalation through the mouth when pressure is supplied in the interface, the mouth seal being formed in one piece with the cushion; and
- a one-way air path in air communication with the interface and with the mouth seal, wherein the one-way air path allows exhausted air from the mouth seal to pass into the interface, but prevents the pressurized gas from the interface from passing into the mouth seal.

30. A mask system, comprising:
- an interface adapted to deliver pressurized gas to a patient's nasal airways;
- a mouth seal adapted to seal with the patient's mouth, to prevent inhalation through the mouth when pressure is supplied in the interface, and provide an effective seal without applying excess rearward force to the patient's jaw; and
- a one-way air path in air communication with the interface and with the mouth seal, wherein the one-way air path allows exhausted air from the mouth seal to pass into the interface and equalize pressure between the interface and the mouth seal, but prevents the pressurized gas from the interface from passing into the mouth seal.

31. The mask system according to claim 30, wherein the excess rearward force displaces the patient's lower jaw to reduce the size of the patient's airway.

* * * * *